(12) United States Patent
Michels

(10) Patent No.: US 10,920,243 B1
(45) Date of Patent: Feb. 16, 2021

(54) METHODS AND ORGANISMS TO ELUCIDATE BIOPOLYMER/SMALL MOLECULE INTERACTIONS

(75) Inventor: William J. Michels, San Rafael, CA (US)

(73) Assignee: Biotica Research Corp., San Anselmo, CA (US)

( * ) Notice: Subject to any disclaimer, the term of this patent is extended or adjusted under 35 U.S.C. 154(b) by 0 days.

(21) Appl. No.: 12/807,274

(22) Filed: Aug. 31, 2010

(51) Int. Cl.
*C12N 15/85* (2006.01)

(52) U.S. Cl.
CPC ...... *C12N 15/8509* (2013.01); *A01K 2217/05* (2013.01); *A01K 2227/105* (2013.01)

(58) Field of Classification Search
CPC .............................................. A01K 2227/703
See application file for complete search history.

(56) References Cited

PUBLICATIONS

U.S Congress (1993, Office of Technology Assessment, Biopolymers: Making Materials Nature's Way, pp. 1-80).*
Touhara et al. (2009, Annu. Rev. Physiol., vol. 71, pp. 307-332).*
Bargmann et al. (1990, Cold Spring Harbor Symposium on Quantitative Biology, vol. LV, pp. 529-538).*
Troemel et al., 1997, Cell, vol. 91, pp. 161-169).*
O'Brochta et al., 2008, Transgenesis and the Management of Vector-Borne Disease, pp. 1-18.*
Rocha et al. 2004, Mar. Biotech., vol. 6, pp. 118-127.*
Nieman et al. 2007, Reproduction, Fertility and Development, vol. 19, pp. 762-770.*
Ristevski S., 2005, Molecular Biotechnology, vol. 29(2), pp. 153-163.*
Sengupta et al. (1996, Cell, vol. 84, pp. 875-887).*
Riddle et al. (1997, C. Elegans II, 2nd Ed., Cold Spring Harbor Laboratory Press, Section II, Induced Mutations).*
Sengupta P. (2007, Pflugers Arch—Eur. J. Physiol., vol. 454, pp. 721-734).*

* cited by examiner

Primary Examiner — Thaian N. Ton
Assistant Examiner — David A. Montanari
(74) Attorney, Agent, or Firm — Jenkins, Wilson, Taylor & Hunt, P.A.

(57) ABSTRACT

Methods for elucidating biopolymer interactions with known and/or unknown small molecules (e.g. candidate drug compounds) are disclosed. These methods utilize novel (usually motile) organisms transformed with one or more heterologous biopolymer sequences. Biopolymer expression is promoted in cells mediating movement in said organism, generally dually-promoted in paired sets of cells mediating oppositely-directed movement. Modulation of motility in the resultant organism due to the presence of small molecules demonstrates small molecule interaction with said natural and/or mutated biopolymer. Analyzed in a chemical gradient, one or more interacting small molecule species can be identified by oriented migration, even in the presence of one or more non-interacting small molecule species. A competing and/or interfering biopolymer can be introduced without obscuring the motility signal. Methods described herein have utility for the discovery of novel therapeutic compounds (drug discovery), for the improvement of existing therapeutic compounds (drug refinement), and for the precise identification of small molecule binding sites on biopolymers via mutagenesis (structural elucidation). A specific embodiment, a Nematode Olfaction-based Structural Elucidation (NOSE) assay, is described herein.

7 Claims, 7 Drawing Sheets

METHODS AND ORGANISMS TO ELUCIDATE BIOPOLYMER/SMALL MOLECULE INTERACTIONS

CROSS REFERENCE TO RELATED APPLICATIONS

Not applicable.

FEDERALLY SPONSORED RESEARCH

Not applicable.

SEQUENCE LISTING OR PROGRAM

Table of Abbreviations in appendix.

BACKGROUND OF THE INVENTION

Field of Invention

Methods for elucidating biopolymer interactions with known and/or unknown small molecules (e.g. candidate drug compounds) are disclosed. These methods utilize novel motile organisms transformed with one or more heterologous biopolymer sequences. Biopolymer expression is promoted in cells mediating movement in said organism, generally dually-promoted in paired sets of cells mediating oppositely-directed movement. Modulation of motility in the resultant organism due to the presence of small molecules demonstrates small molecule interaction with said natural and/or mutated biopolymer.

Related Disclosures.

The ability to determine non-covalent interactions between molecules is a fundamental methodology in the basic sciences. In biological systems, elucidating the presence and strength of these interactions is critical to understanding the function of polypeptides, nucleic acids, enzymes, sub-cellular structures, cells, tissues, and organ systems. The exogenous addition of chemical compounds to biological systems and/or biopolymers in vivo and in vitro has proven useful both scientifically and therapeutically, by assisting in understanding normal cellular function, and by identifying compounds that can alleviate cellular and organismal dysfunction. Thus methods that can rapidly elucidate interactions between small molecules and biopolymers are highly desired in the art.

Assays for small molecule/biopolymer interactions generally fall into two classes: cellular assays and cell-free assays. Cellular assays can report on changes in cellular function in response to chemical treatment. A classic example is treatment of *E. coli* with IPTG (inducer) and X-gal (chromogenic substrate) to produce a blue precipitate upon cellular induction of the Lac Z gene (beta-galactosidase).

Cell-free assays can report on changes in biochemical structure and function. A classic example is the use of nitrophenyl phosphate-labeled compounds to monitor the presence and activity of phosphatase(s) in an in vitro assay. The presence of small molecule phosphatase inhibitors/activators can be easily assayed chromogenically.

A large gap exists between these two disparate techniques. Cellular assays can demonstrate small molecule interactions acting through defined genetic pathways involving dozens of gene products (e.g. teratogenic assays), however determining which gene product is directly affected by small molecule activation/inhibition is often problematic. Cell-free assays can demonstrate small molecule activation/inhibition at the level of a single active site (within a single gene product) using classic enzymological techniques, however small molecule activators/inhibitors identified in this manner may have no effect at the cellular level, because other gene products in a pathway are rate-limiting. Both cellular and cell free assays (e.g. assays containing cellular extract) suffer from the presence of interfering and/or inhibiting factors, which can skew binding data and/or obscure the identification of novel drug targets and therapeutic compounds. The presence of interfering and/or inhibiting factors often necessitates careful and/or time-consuming choice of heterologous expression systems (cellular assays), or careful and/or time-consuming purification steps (cell-free assays).

Cellular assays are useful for determining general chemical properties pertaining to biological systems, but not readily useful for deciphering chemical interactions with specific cellular components. An example of a general assay is the classic Ames mutagenesis test. Other cellular assays are designed to fluorescently determine cellular cytotoxicity, cellular oxidative/reductive state, cellular adhesion, cellular cell-cycle state, and/or cellular apoptosis. These assays are employed to study cells alone, cells modified by molecular methods (transformation and/or gene disruption), or cellular responses to added exogenous chemical(s). Because the traits listed are determined multigenically, it is difficult to discern which cellular components (e.g. biopolymers) are affected by added exogenous chemical.

Cell free assays in widespread use are often more appropriate for large biopolymer identification, than for identification of small molecule binding interactions. Antibody-based assays such as enzyme-linked immunosorption assays (ELISA) are designed to detect the presence and identity of large biopolymers. While small molecule activators/inhibitors can identified using ELISAs, obtaining precise binding data for such small molecules is labor intensive and may require costly development of numerous high quality antibodies with low cross-reactivity.

Recent developments in the field have sought to develop methods of analysis that bridge the gap between cellular and cell free assay methods. For example, an advanced cellular technique known as the yeast "two-hybrid" system allows for the identification of specific protein-protein interactions between two gene products. Briefly, two closely opposed protein domains involved in DNA transcription—domains that normally interact by protein/protein binding—are each replaced with heterologous sequence (i.e. creating two hybrid proteins). If cellular activation of a reporter gene is observed, the two heterologous sequences must interact (i.e. bind each other in vivo). Unknown binding partners can be selected and identified due to the ease with which thousands of yeast clones are created and manipulated in the laboratory. Interfering and/or inhibiting factors are minimized because the two hybrid proteins are held in close opposition during transcriptional activation. This technique has been adapted to identify protein/RNA interactions, and to identify small molecule "activators" (i.e. agonists) and "disruptors" (i.e. antagonists).

Regarding use of this technique to identify small molecule inhibitors/activators, the yeast two-hybrid system has a number of shortcomings. Like cell-free assays, small molecule inhibitors/activators isolated by this technique may have no effect at the cellular level; the cell may contain multiple binding partners for a particular effector protein, only one of which is inhibited by the small molecule isolated. Unlike cell free assays, whole gene products are typically not analyzed in the two hybrid system: only short protein domains are studied. While this property might appear to be an advantage, e.g. by providing precise localization of small molecule binding sites within protein domains, in fact this property may be a disadvantage for small molecule/biopolymer analysis. Small molecules can interact with biopolymers in three classic modalities: competitive interaction, non-competitive interaction, and uncompetitive interaction. Because only short protein domains are studied, small molecule activators and disruptors identified by the two hybrid system may be restricted to the class of competitive inhibitors, i.e. small molecules that compete for binding with the normal proteinaceous binding partner.

The yeast two hybrid system is fundamentally designed to elucidate protein/protein binding interactions. Therefore classes of small molecules that act on a single protein to effect allosteric change may not be identified using this assay, because binding partners are required to perform the assay. Finally, because the assay fundamentally measures in vivo binding, the yeast two hybrid system may fail to recover small molecule inhibitors/activators of enzymatic activity, such as active site or 'suicide' inhibitors, since enzymatic activity and/or inhibition is not an intrinsic measurement of the assay.

Numerous cell-free assay systems have been designed to obtain structural and/or small molecule binding data for user-defined biopolymers. Despite their elegant design, a drawback of cell-free assays is the time and complexity of designing hundreds (or even thousands) of different assays to test the activity of each different biopolymer. For example, a study of transposase may entail an assay designed to ascertain the insertion or excision of foreign DNA into/from a model DNA substrate. Structure/function analysis can be performed by mutating the enzyme, the substrate, or both. Small molecule inhibitor/activator data can be obtained for unmutated enzyme, mutated enzyme, and/or substrate. However, an entirely different assay must be designed to analyze another nucleic acid modifying enzyme, a restriction endonuclease. A standardized 'output' for assays would be highly desired in the art.

Because of the in vitro nature of these assays, entire classes of biopolymers are difficult to study by cell-free assay, such as membrane proteins. Cell free assays encounter difficulties in vitro production of biopolymers, and/or denaturation of biopolymers. In recognition of these facts, user-defined cellular assays have been designed for the analysis of biopolymers difficult to study by other methods. Heterologous cellular expression systems have been designed to identify novel biopolymers, and to obtain structural and small molecule binding data. For example, in one of the most advanced methodologies available, known or unknown gene products mediating ionotropic or metabotropic responses can be expressed heterologously in *Xenopus* oocytes by micro-injection of heterologous mRNA, and electrophysiological assays employed to test for the presence of novel proteinaceous receptors. Further experimentation can identify small molecule agonists and antagonists of receptor function. A single assay method, e.g. whole cell or patch clamp electrophysiological assay, has become an alternative to multiple different assays.

A difficulty with the heterologous expression technique in *Xenopus* oocytes is robustness: heterologous expression in *Xenopus* oocytes is sensitive to a multitude of experimental conditions (oocyte age, oocyte condition, mRNA quality, mRNA degradation or decay, duration of expression, temperature, ionic condition, competing cellular factors, prior exposure, etc.). Heterologous expression is demanding in terms of experimenter training and equipment (e.g. patch clamp electrophysiological analysis). *Xenopus* oocytes cannot be grown in culture but must be isolated; injected oocytes cannot be maintained as a self-reproducing strain. Analysis of small molecule agonists and antagonists is most often performed serially, limiting the number of data points that can be collected. These properties obviate massively-parallel implementation of *Xenopus* oocyte-based heterologous expression as a method adaptable for intensive, high-throughput structure/function analysis, or for drug discovery. A robust method for elucidating binding interactions between small molecules and biopolymers, requiring less demanding expertise and less high quality instrumentation, and capable of being implemented on a massively-parallel scale, would be highly desired in the art.

A shortcoming of all methods described herein is the difficulty of obtaining complete, precise, atomic-level resolution of binding sites on biopolymers where small molecules bind. Often to obtain precise binding information of this quality, a researcher must resort to physiochemial analysis. To analyze binding of small molecules to large biopolymers, physiochemical analysis includes nuclear magnetic resonance (NMR) studies or X-ray crystallographic studies, at substantial expenditure of time, materials, and equipment.

Objects and Advantages.

Novel Methods for Elucidating Biopolymer/Small Molecule Interactions.

Overview.

A motile biological organism (i.e. an organism comprising a motility system) is manipulated to detect a known or unknown small molecule (chemical compound). Said biological organism is manipulated in the laboratory to express a biopolymer (e.g. a proteinaceous receptor) in a paired set of mediators: detection is based on alteration of organism motility (see FIG. 1). A key requirement of the methods herein is that an organism's motility system comprises separate mediators (e.g. cells or neurons) directing movement. Mediators may comprise cells (e.g. neurons), neural circuits (e.g. mechanosensory circuits, chemosensory circuits), or neural systems (e.g. reflex responses, chemosensory attraction and/or repulsion, mechanosensory attraction and/or repulsion). Generally these mediators are paired and direct movement in opposite directions, such as forward-directed movement and backward-directed movement (anterior/posterior movement), although any two such distinguishable mobility changes can be utilized (e.g. turning left vs. right, turning up vs. down, etc.)

Novel Properties.

An unanticipated result of biopolymers expressed as described (e.g. heterologous expression of the same biopolymer in cells directing motility in opposite directions or in detectably different manners) is that organisms so manipulated can be tested to a) identify unknown biopolymers interacting with known drugs, and b) identify novel small molecules that interact with a known biopolymer, such as a proteinaceous receptor. For example, an assay comprises heterologous expression of the same biopolymer in cells directing motility in opposite directions. By simultaneously activating both mediators (e.g. circuits), an interacting small molecule will cause immobility in a freely motile organism (see FIG. 2). As a second example an assay comprising a constituitively active receptor intracellular domain is expressed such that the organism is immobilized; a novel small molecule antagonist can thus be identified which inhibits immobility, allowing movement. Traditional assays and/or single transgene expression can be subsequently used to determine the type of biomolecular interaction, e.g. if said small molecules activates a given biopolymer ("activators" or "agonists") or inhibits a given biopolymer ("inhibitors" or "antagonists"). This embodiment is useful for discovering novel therapeutic agents.

A second unanticipated result of expression as described herein is that expression of identical biopolymers one of which has been altered by application of mutagenesis methods known in the art (e.g. site-directed mutagenesis, chimeragenesis, etc.) enables precise, atomic-level mapping of small molecules to biopolymers (such as membrane-traversing receptors) via the same motility assay, without resorting to physiochemical analysis such as nuclear magnetic resonance (NMR) or X-ray crystallography (see FIG. 3 and FIG. 4). The method takes advantage of biomolecular differences, such as differential binding affinities between said small molecule and so-called 'wild-type' and 'mutant' biopolymers, resulting in a movement phenotype that can be easily scored. In numerous embodiments, mutagenesis and/or chimeragenesis techniques known in the art can be used to create such "allelic pairs," or alleles can be recovered from populations and assayed as described. The methods described herein can be used to a) generate structural interaction maps for known drugs or b) to isolate novel therapeutics interacting at known sites. Standard enzymological techniques known in the art (e.g. kinetic and/or electrophysiological analysis) can then be used to confirm drug identification or biochemical effect of mutation of activity.

A third unanticipated result of expression as described is that organisms expressing dissimilar biopolymers in each class of motility mediator (e.g. sensory neuron) solves a problem inherent in both cellular and cell free assay systems: small molecules that activate or inhibit a pre-determined (user-defined) biopolymer can be identified in the presence of a second pre-determined (user-defined) biopolymer, and activity on each biopolymer differentiated (see FIG. 5). For example, a rare receptor sub-type can be analyzed in the presence of a highly expressed receptor, obviating interference that occurs in traditional assays. Alternatively chemical compounds modulating interactions between two biopolymers in a signal transduction pathway can be recovered by co expressing the two different biopolymers, e.g. an upstream activating biopolymer in a cell directing forward movement and a downstream effector in a cell directing reverse movement, in the same test organism. The organism would have altered mobility such that the it would be wholly dependent upon the activated upstream gene: chemical compounds can be recovered in a single assay that either a) inhibit the activating upstream gene relative to the endogenous signalling apparatus (i.e. an anti cancer agent) or b) activate the downstream effector gene relative to the endogenous signalling apparatus (i.e. to correct a human homozygous deficiency in the upstream gene), or both. This embodiment enables identification of high quality therapeutic agents (drug refinement). Furthermore, this embodiment enables recovery highly-specific drug candidates against human genes that can be accomplished for known genes that have little to no mutational data, or an unsuitable mutant repository (i.e. drugs to correct loss-of-function upstream genes are required but cells/animals are inviable).

A fourth unanticipated result of expression as described is that organism containing dually mutated and/or recombined biopolymers enables drug discovery at user-defined sites different from known sites of chemical interaction (see FIGS. 6 and 7). For example, biopolymers dually-mutated at a site of known drug interaction (e.g. via mutagenesis) enables scoring of novel drug interactions by the prior genetic ablation of known drug interaction sites. Alternatively mutagenesis of distantly-related biopolymers, e.g. by terminal truncation, nested deltion, or reciprocal exchange, can be used to identify the site or sites of action of known or novel drugs on each. This embodiment enables isolation of novel and/or adjuvant therapeutics, therapeutics that can be used alternatively and/or in addition to and/or in combination with pre-existing therapeutic agents.

Exemplary Embodiments.

Organisms are dually-transformed such that one or more biopolymers are heterologously expressed in paired mediators (e.g. cells, neurons), as described (see FIG. 1). In an exemplary embodiment, said motility system comprises chemoattractive and chemorepulsive cells within a nervous system (i.e. cells responsible for mediating sensation of small molecules and generating appropriate chemoattractive and chemorepulsive responses). Chemoattractive and/or chemorepulsive cells are defined herein as cells that respond to either soluble chemical compounds or volatile chemical compounds, or both soluble chemical compounds and volatile chemical compounds. In a second exemplary embodiment, one or more paired sets of non-sensory cells capable of directing movement in opposite directions (or detectably different manners) are manipulated in the laboratory to mediate sensation of known or unknown small molecules (see FIG. 1). Example of such a paired set of non-sensory cells include paired sets of agonistic and antagonistic inter neurons and/or motor neurons. Cells mediating an attractive response are abbreviated "A" cells or "A" mediators (see diagrams). Cells mediating a repulsive response are abbreviated "R" cells or "R" mediators (see FIGS. 1-7).

Candidate Organisms.

Most typically the methods described herein are performed using strains of the nematode *Caenorhabditis elegans*. Other organisms amenable to study include other transformable species of nematodes, as well as transformable species of slime mold, hydra, insect, fruit fly, honey bee, fish, amphibian, reptile, bird, rodent, non-human mammals, etc., or any other transformable, motile, non-human organism containing identified, distinct (normally cellular) mediators (e.g. neurons) directing movement in opposite directions or distinguishable manners, such as chemoattractive and chemorepulsive behavior, and with known, distinguishable promoters capable of expression within each mediator (e.g. cell) directing such movement.

A. Immobility induced in the presence of exogenously-applied chemical ligand indicates ligand-dependent biomolecular coupling to the endogenous locomotory circuitry (see FIG. 2 and Table 5). Biopolymers of this class are referred to as 'ligand-coupled' and interacting small molecules can be recovered using the assay described in FIG. 2 in the presence or absence of a known ligand. Ligand-coupled biopolymers either activate or inhibit the endogenous locomotory circuitry, and can be differentiated by assays below.

B. Immobility induced in the absence of a known exogenously-applied chemical ligand indicates biomolecular coupling to the endogenous locomotory circuitry (see Tables 5 and 6). Biopolymers of this class are referred to as 'intrinsically coupled' and interacting small molecules can be recovered using the assay described in FIG. 2. Intrinsically-coupled biopolymers either activate or inhibit the endogenous locomotory circuitry and can be differentiated by assays below. Intrinsically coupled biopolymers that act on cellular effectors of mobility, e.g. endogenous signal transduction components, are thus known as 'cellular-dependent' intrinsically-coupled biopolymers. Intrinsically-coupled biopolymers can act independently of cellular effectors of motility, e.g. a mutant channel that causes cellular depolarization, and are thus called 'cellular-independent' intrinsically-coupled biopolymers (see Table 8).

Figure 1:
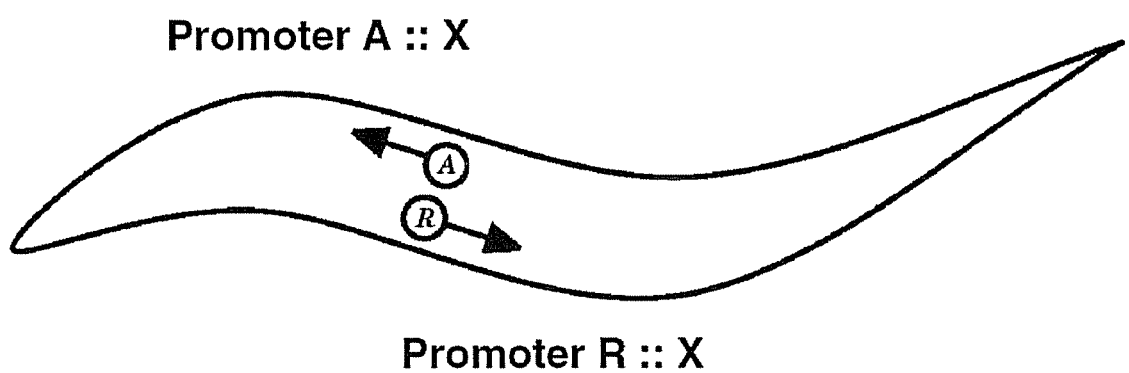
FIG. 1 Embodiment: user-defined gene X expressed such that a biopolymer X encoded by gene X simultaneously modulates motility in opposite or nearly opposite directions (+/−additional small molecule modulation). Briefly, a transgenic animal is constructed whereby expression of gene X is controlled by promoters designed to express gene X biopolymer in mediators of movement (e.g. cells, neurons) that direct motility in opposite or nearly opposite directions. The circle containing the letter A represents "cell A", a cell or neuron that controls forward movement. The circle containing the letter R represents "cell R", a cell or neuron that controls reverse (or backward) movement. According to convention, the double-colon represents a gene operatively linked to a promoter. In this case gene X is operatively linked to Promoter A, which expresses gene X in cell A, a mediator of attractive and/or forward movement (e.g. a chemoattractive neuron). In this case gene X is operatively linked to Promoter R, which expresses gene X in cell R, a mediator of repulsive and/or reverse movement (e.g. a chemorepulsive neuron). This diagram represents a basic transgenic embodiment. Biopolymers amenable to study include peptides, polypeptides, full length proteins, as well as structural RNA molecules, i.e. RNA molecules such as microRNAs (miRNA) and small interfering RNAs (siR-NAs).
Figure 2:
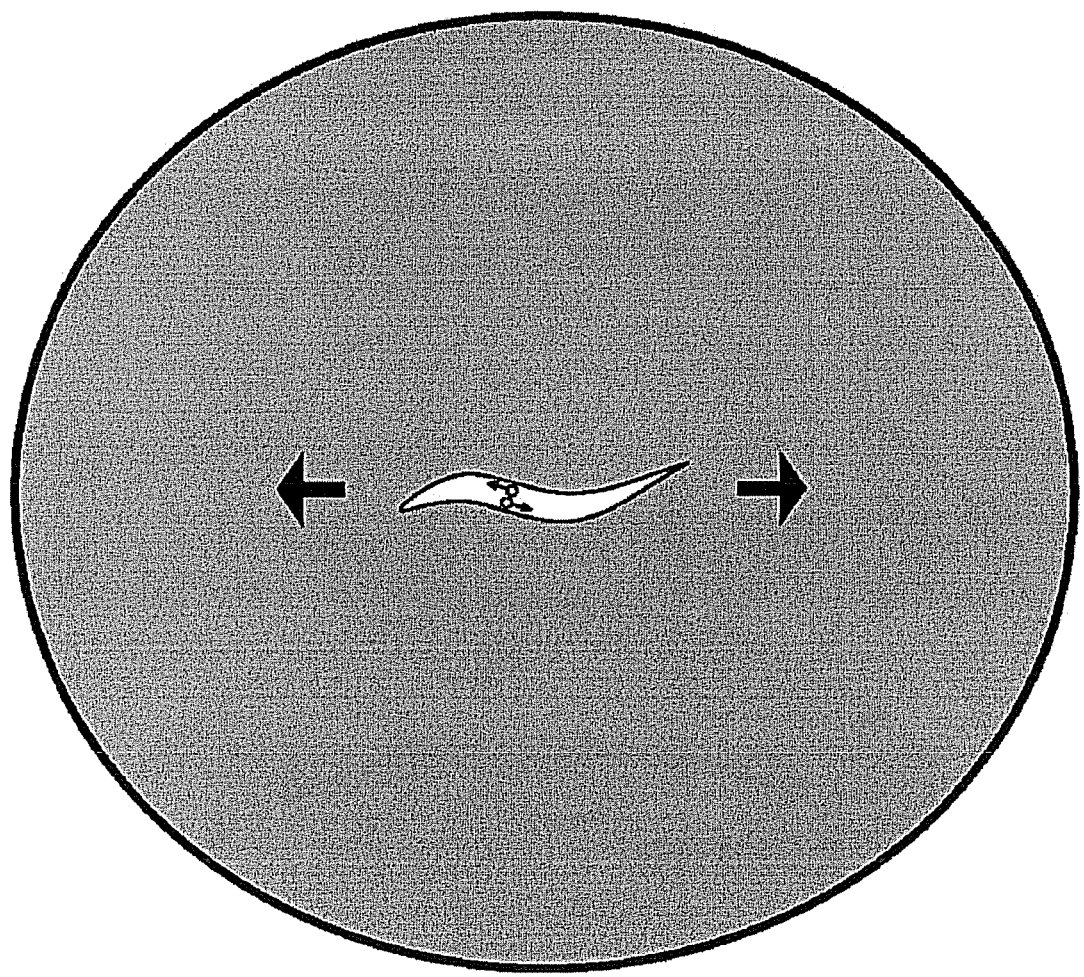

FIG. 2 Embodiment: user-defined organism/biopolymer employed to identify a chemical (i.e. a novel therapeutic drug) via chemical-induced mobility changes, i.e. from immobile to mobile or vice versa. (uniform chemical field indicated in grey). In this general embodiment, a small molecule (chemical compound) surrounds the transgenic organism described in FIG. 1. The small molecule is present at approximately equivalent concentration in the assay field, i.e. no gradient is present. Changes in motility behavior include a change from free, undirected movement to immobility+/−rapid oscillation between forward-directed and backward directed movement, or vice versa. An assay as described in this embodiment may be employed to demonstrate that a compound interacts with a user-defined biopolymer (i.e. drug confirmation) without resorting to cell free assays, or cellular assays such as electrophysiology. An assay as described in this embodiment may be employed to identify a previously unknown compound causing the observed immobility (i.e. drug discovery). An assay as described in this embodiment may be employed to isolate a single homogeneous compound causing the observed immobility from a mixture of numerous compounds (i.e. drug isolation).

A. In a 'ligand-coupled' embodiment, the presence of a small molecule that interacts with the user-defined biopolymer (e.g. gene X biopolymer) is detected by induced immobility: the normally motile organism becomes immobile or nearly immobile in a uniform field of ligand. For example, the expression of identical neurotransmitter receptors in each of the attractive (forward) and repulsive (reverse) directing cells induces immobility when exposed to cognate neurotransmitter (Table s 4 and 5). Assays useful for detecting unknown small molecules test for 1. induced immobility in the absence of known neurotransmitter ligand (e.g. competitive agonists), 2. induced immobility in the presence of known neurotransmitter ligand (e.g. competitive or non-competitive antagonists).

B. In an 'intrinsically-coupled' embodiment the test organism is a priori immobile by virtue of transgene expression. The presence of a small molecule that interacts with the user-defined biopolymer (e.g. gene X biopolymer) is detected by induced mobility: the immobile organism becomes mobile in a field of known or unknown interacting small molecule chemical compounds (Tables 2 and 3). For example, the expression of identical mutant activated G-alpha-s subunit in each of the attractive (forward) and repulsive (reverse) directing cells induces immobility in the absence of external chemical stimulus. An assay useful for detecting unknown ineracting small molecules tests for induced mobility (e.g. competitive or non-competitive G-alpha-s antagonists are recovered).

Figure 3:
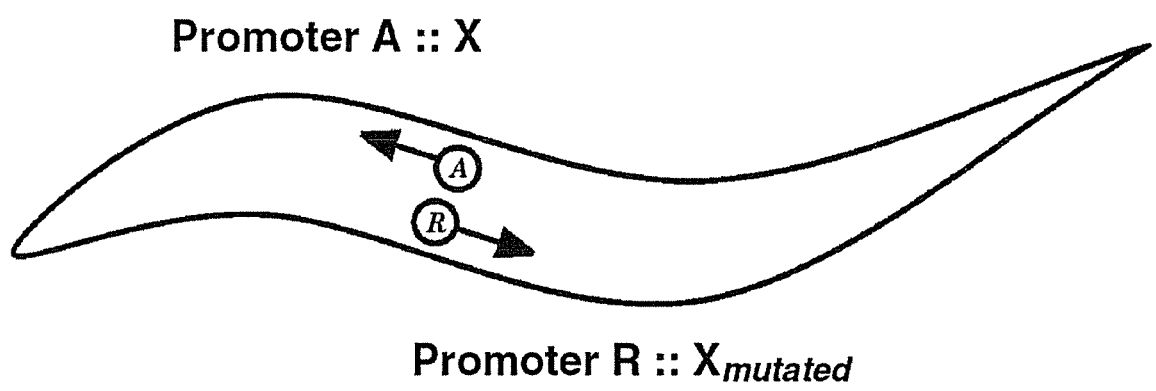

FIG. 3 Embodiment for determining site-specific interaction(s) between one or more small molecule(s) and biopolymer X. Briefly, a transgenic strain is constructed as in FIG. 1 excepting that biopolymer X expressed from one of the two expression constructs has been mutated. In some embodiments mutagenesis is performed prior to transgenesis. In some embodiments mutagenesis is performed on a strain as, described in FIG. 1. In some embodiments mutagenesis is site-specific (also known as site-directed). In some embodiments mutagenesis is random or pseudo-random. In some embodiments a site of mutagenesis is known a priori. In some embodiments, sites of mutagenesis are unknown. In some embodiments, mutagenesis reveals an alleviation of immobility as described in FIG. 2. Site-specific interactions are mapped by correlating site(s) of mutagenesis with changes in mobility.

Figure 4:
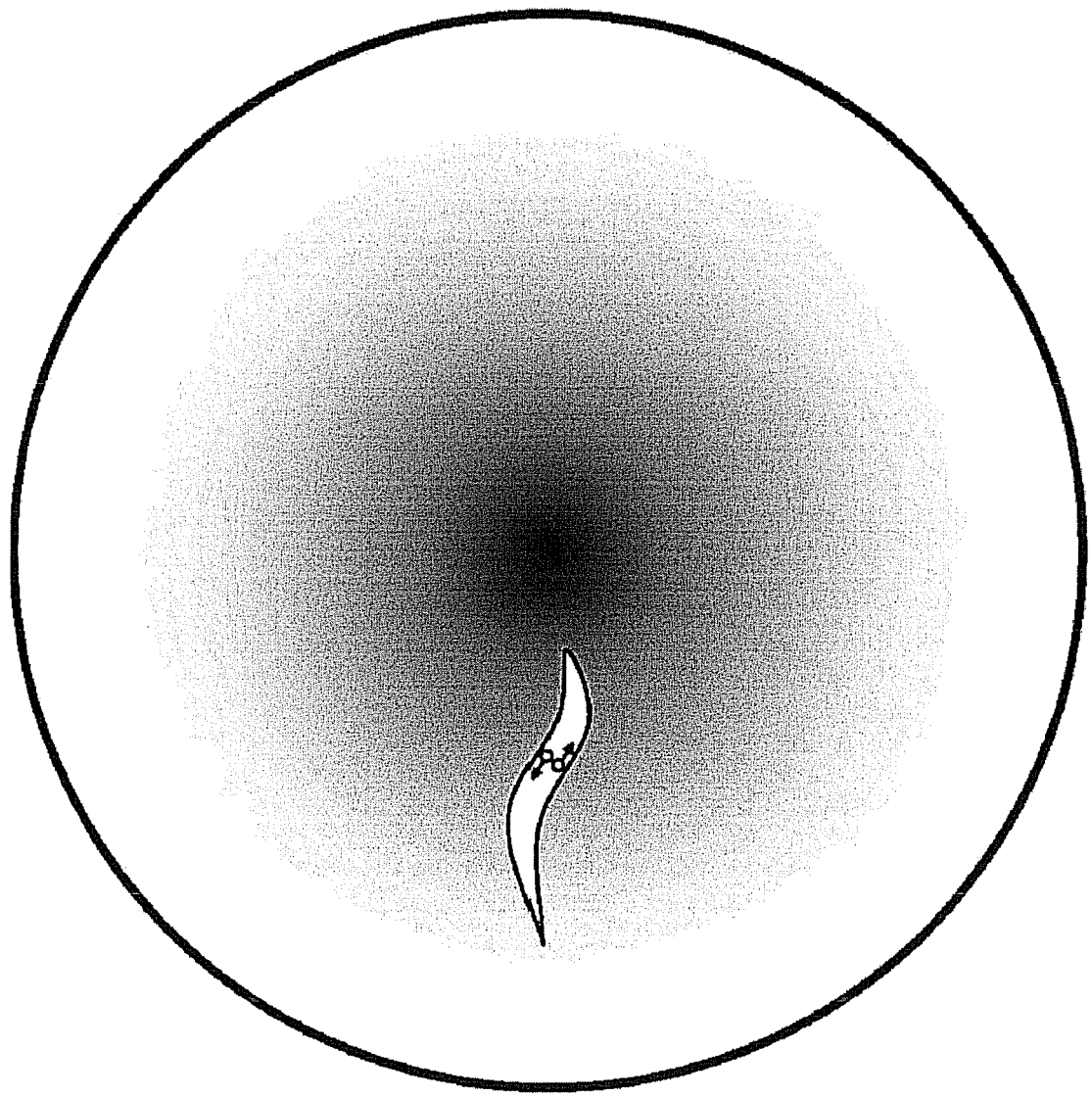

FIG. 4 User-defined "heterozygous" organism employed to identify a chemical (e.g. a novel drug), and/or to elucidate biopolymer—chemical interactions (e.g. using chemical gradient shown in grey—black). In this embodiment, a transgenic organism as described in FIG. 3 is placed in a gradient of small molecule (chemical compound). Detection of a small molecule interacting with biopolymer X would normally result in immobility as demonstrated in FIG. 2. Introduction of a mutation into one construct expressing biopolymer X alleviates immobility if the mutation alters a site of biopolymer/small molecule interaction. Unknown sites of biopolymer/small molecule interactions can be identified in this manner. The manner of interaction (e.g. activation and/or inhibition) can be predicted from known parameters (e.g. location of mutated biopolymer, direction of mobility, etc.) and/or the construction of control strains as in FIG. 1 and FIG. 6. Interpretation in Tables 9, 10 and 11.

Figure 5:
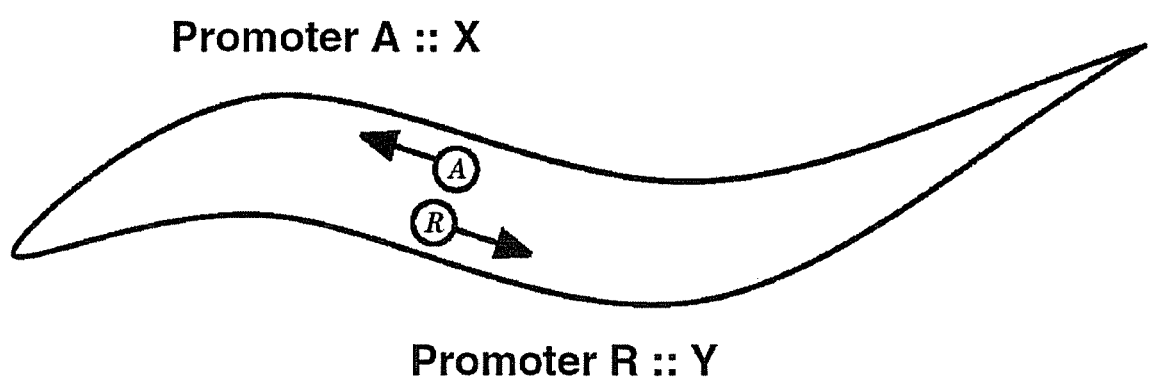

FIG. 5 User-defined organism for detecting one or more small molecule species (e.g. therapeutic drugs) interacting with either biopolymer X or Y, despite the presence of the other biopolymer. Briefly, a biopolymer such as biopolymer X may be placed in a cell or cells directing chemoattractive movement ("cell A"). Addition of a small molecule agonist (activator) induced mobility towards the source of the chemical, when assayed in a gradient as described in FIG. 4. This mobility can only occur if the small molecule does not have a similar effect on biopolymer Y, expressed in a cell ("cell R") directing chemorepulsive movement. Highly specific therapeutic compounds can be isolated in this manner, compounds that have reduced toxicity and/or side-effects. Interpretation in Tables 12 and 13.

Figure 6:
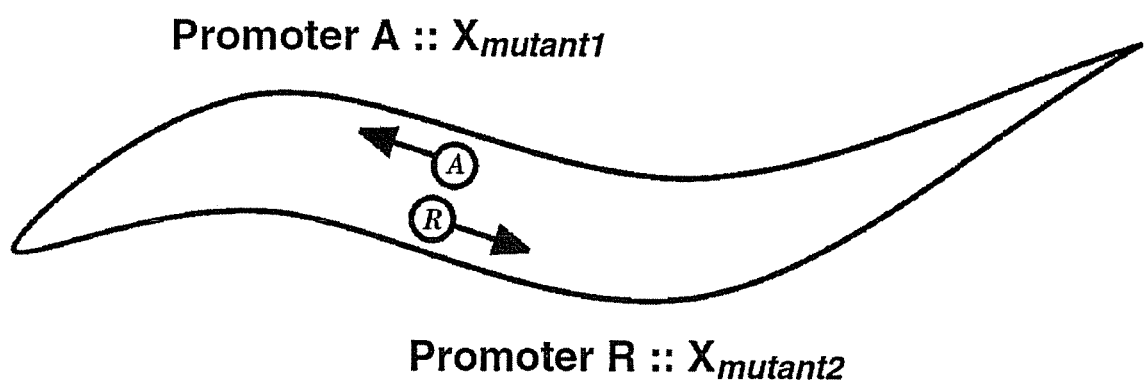

FIG. 6 User-defined organism comprising dual mutagenized and/or recombined expression useful for analyzing biopolymer structure/function+/−small molecule modulator(s). In this embodiment, changes to a given biopolymer ("biopolymer X") can be compared directly with each other in a "heteroallelic" style assay. For example, a single site on a biopolymer can be tested to see which of the twenty standard amino acids are most effective at contributing to a biochemical function, e.g. modifying an ion channel to alter its existing selectivity filter for use in making highly-selective recombinant biosensors. Alternatively, this embodiment can be used to isolate bioactive compounds that are active at sites different from known sites of interaction (see text).

Figure 7:
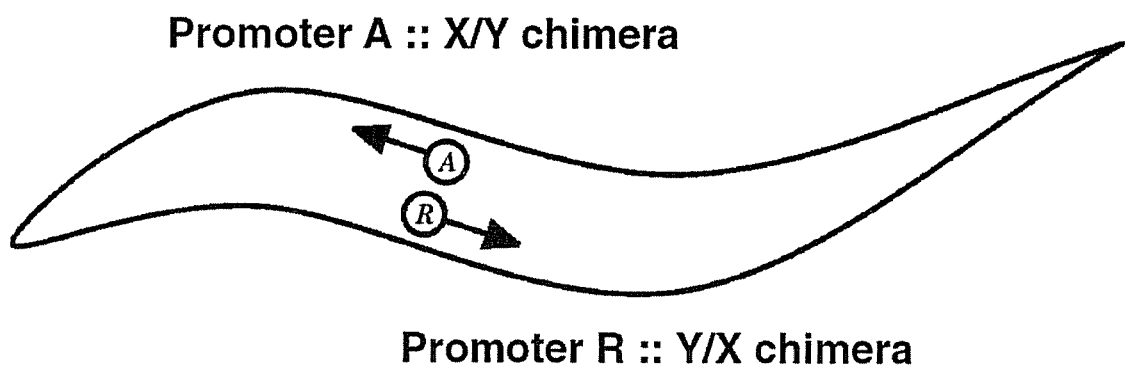

FIG. 7 Embodiment for mapping biopolymer elements and/or domains using recombined (e.g. reciprocal chimeric) expression constructs+/−small molecule(s). In this embodiment, closely related, distally related, or unrelated biopolymers are recombined to identify functional elements within recombinant biopolymers. Reciprocal chimeric constructs are made and expressed in mediators of movement as described. Reciprocally exchanged regions that result in significant alterations of mobility functionally identify domains (and/or elements) of the biopolymer(s) important for function, when compared to control strains (e.g. as in FIG. 5). For example, two ion channels within an ion channel superfamily respond differently to applied chemical (agonist or antagonist). Reciprocal exchange of regions of these two biopolymers, biopolymer X and biopolymer Y, can be used to identify region(s) responsible for differential response to chemical (agonist or antagonist).

PRINCIPAL EMBODIMENTS

1. Single Biopolymer Expression.
A. Identical Expression.

Throughout these embodiments, in a conventional nomenclature, defined promoters driving expression of a heterologous gene are designated "Promoter A::Gene X", where the doubled colon indicates that Promoter A fragment is operatively linked to Gene X fragment such that Gene X is expressed under the direction and control of Promoter A (see diagrams). Furthermore, as demonstrated in the art, genes encode biopolymers such as microRNAs (miRNAs), small interfering RNAs (siRNAs), structural RNAs (e.g. spliceosomal or ribosomal RNAs), peptides, polypeptides, and proteins. Throughout these embodiments, the words "biopolymer" and "receptor" are used interchangeably, a receptor representing a biopolymer that may be analyzed by the methods herein. A representative listing of known chemosensory cell types from the nematode *C. elegans* is listed below in Table 1. Generally one promoter is chosen from each chemosensory class, e.g. one chemoattractive promoter and one chemorepulsive promoter from Class 1 to generate a transgenic animal.

TABLE 1

| Chemosensory cell-types and Promoters | | | | |
|---|---|---|---|---|
| | Cell-types | Gene name | Gene Promoter | Wormbase Expression pattern |
| Chemo-attractive cell type Class 1 | AWA, AWC | odr-10 odr-7 | C53B7.5 T18D3.2 | Expr280 Expr282 |

TABLE 1-continued

| Chemosensory cell-types and Promoters | | | | |
|---|---|---|---|---|
| | Cell-types | Gene name | Gene Promoter | Wormbase Expression pattern |
| Chemo-repulsive cell type Class 1 | AWB, ASH, ADL | osm-9 sra-6 | B0212.5 AH6.10 | Expr285 Expr296 |
| Chemo-attractive cell type Class 2 | ASE, ADF, ASG, ASI, ASK | gcy-5 gcy-6 gcy-7 srd-1 sra-7 sra-9 srg-2 srg-8 | ZK970.6 B0024.6 F52E1.4a F33H1.5 AH6.11 AH6.14 C18F10.5 T12A2.9 | Expr238 Expr239 Expr240 Expr302 Expr297 Expr298 Expr300 Expr301 |
| Chemo-repulsive cell type Class 2 | ASH, ADL | osm-9 sra-6 | B0212.5 AH6.10 | Expr285 Expr296 |

In a primary embodiment (FIG. 1), sensory cells are manipulated to express identical biopolymers in one or more paired sets of sensory cell directing opposing movement ("push-me-pull-you" embodiment). In the absence of small molecule effectors, a dually-transformed strain is made immobile by the expression of identical biopolymers in cells as described (Table 2, top strain). Biopolymers inducing immobility are said to 'couple' to the endogenous locomotory pathway and/or gene products, and are amenable for further study by the methods described herein. Biopolymers that do not intrinsically couple to the endogenous locomotory pathway are shown (Table 2, bottom strain).

TABLE 2

| Dual transformation quick coupling assay. | | | |
|---|---|---|---|
| Attractive Cell | Repulsive Cell | Pheno-type | Molecular Interaction |
| Biopolymer X (wild-type) | Biopolymer X (wild-type) | Immobile | Biopolymer X couples to endogenous locomotory circuitry |
| Biopolymer X (wild-type) | Biopolymer X (wild-type) | None (wild type) | Biopolymer X does not couple to endo-genous locomotory circuitry |

In a dual transformed test organism, teh heterologous gene product can couple to the locomotory circuitry in two manners, either positively or negatively. For example, a heterologous kinase may act positively and promote locomotion, while a heterologous phosphatase may act negatively and inhibit locomotion. Table 3 outilnes the construction of single-promoter control strains to differentiate positively acting heterologous biopolymers ("loco-pos") versus negatively acting heterologous biopolymers (loco-neg").

TABLE 3

Differentiating positively acting heterologous biopolymers from negative.

| Attractive Cell | Repulsive Cell | Phenotype | Sign of molecular Interaction |
|---|---|---|---|
| Biopolymer X (wild-type) | Biopolymer X (wild-type) | Immobile | Biopolymer X couples to endogenous locomotory circuits |
| Biopolymer X (wild type) | | Increased forward locomotion vs. wild-type | Biopolymer X couples positively to endogenous forward locomotory circuitry (loco-pos) |
| | Biopolymer X (wild type) | Decreased forward locomotion vs. wild-type | Biopolymer X couples positively to endogenous reverse locomotory circuitry (loco-pos) |
| Biopolymer X (wild type) | | Decreased forward locomotion vs. wild-type | Biopolymer X couples negatively to endogenous forward locomotory circuitry (loco-neg) |
| | Biopolymer X (wild type) | Increased forward locomotion vs. wild-type | Biopolymer X couples negatively to endogenous reverse locomotory circuitry (loco-neg) |

Intrinsically non-coupling biopolymers are analyzed by the methods described herein with by the addition of known ligands. For example, many gene products will fail to signal in the absence of known ligand. Some of the gene products (biopolymers) will not be amenable for further study (see Table 4 below).

TABLE 4

Heterologous biopolymers uncoupled from locomotory circuitry.

| Attractive Cell | Repulsive Cell | Phenotype | Molecular Interaction |
|---|---|---|---|
| Biopolymer X (wild-type) | Biopolymer X (wild-type) | None (wild-type) | Biopolymer X does not couple to endogenous locomotory circuits |
| Biopolymer X (wild type) | | None (wild-type) | Biopolymer X does not couple to forward circuitry (control strain) |
| | Biopolymer X (wild type) | None (wild-type) | Biopolymer X does not couple to reverse circuitry (control strain) |

However many biopolymers may be induced to interact by the addition of known ligand. Neurotransmitter receptors expressed as described are activated by addition of cognate neurotransmitter added to the media. Thus 'non-coupling' biopolymers are made 'coupling' by the addition of known ligand (Table 5), and are amenable to further study as described herein.

TABLE 5

Heterologous biopolymers induced to couple with locomotory circuitry by the addition of exogenous ligand.

| Dually-expressed gene | Phenotype – ligand | Phenotype + ligand | Molecular Interaction |
|---|---|---|---|
| Biopolymer X | freely mobile | induced immobility | "ligand-dependent" (extrinsically) coupled |
| Biopolymer X | immobile | immobile (unchanged) | "ligand-independent" (intrinsically) coupled |

It will be evident from this analysis that exogenous ligand is simply a natural small molecule chemical effector, i.e. a drug. References herein are generally to a small molecule chemical, however sugar-based, carbohydrate-based, lipid-based, nucleic acid-based, peptide-based, polypeptide-based and proteinaceous drugs can also be recovered.

TABLE 6

Intrinsically coupled and extrinsically coupled biopolymer.

| Attractive and/or Repulsive Cell | Phenotype – uniform ligand or drug field | Phenotype + uniform ligand or drug field | Molecular Interaction |
|---|---|---|---|
| Both cells Biopolymer X (wild-type) | None (wild-type) | Immobile | Biopolymer X couples in drug-dependent manner to endogenous locomotory circuits |
| Attractive cell only Biopolymer X (wild type) | None (wild-type) | Increased forward locomotion vs wild-type | Biopolymer X couples positively in drug-dependent manner to forward locomotory circuitry (loco-pos) |
| Repulsive cell only Biopolymer X (wild type) | None (wild-type) | Decreased forward locomotion vs wild-type | Biopolymer X couples positively in drug-dependent manner to reverse locomotory circuitry (loco-pos) |
| Attractive cell only Biopolymer X (wild type) | None (wild-type) | Decreased forward locomotion vs wild-type | Biopolymer X couples negatively in drug-dependent manner to forward locomotory circuitry (loco-neg) |
| Repulsive cell only Biopolymer X (wild type) | None (wild-type) | Increased forward locomotion vs wild-type | Biopolymer X couples negatively in drug-dependent manner to reverse locomotory circuitry (loco-neg) |

Table 6 reiterates the concept of Table 3 in detailing how 'positively' coupled and 'negatively' have different effects in singly-transformed animals. Table 6 provides the framework for drug analysis. For example, a dually transformed animal may be immobile because heterologous genes are positively acting on locomotion, and the organism remains motionless. Alternatively, a dually transformed animal could be inhibited in each cell type by negatively-coupled hetero-polymer, and the animal again remains mothinless. Single-transformation constructs and interpretation are listed in Table 6.

TABLE 7

Specialized strains can can be used to study locomotory effect.

| Dually-expressed gene | Phenotype + cellular effector(s) | Phenotype − cellular effector(s) | Molecular Interaction |
|---|---|---|---|
| Biopolymer X | induced immobility | freely mobile | "cellular-dependent" coupling |
| Biopolymer X | immobile (unchanged) | immobile | "cellular-independent" coupling |

Table 7 shows that some heterologous gene products require cellular effectors to produce locomotory changes, and some do not. Table 8 combines coupling, cellular, and ligand parameters to provide an overall framework for studying heterologous genes in dually-transformed strains, and identifying either novel drugs or novel structural interactions with known ligands and/or drugs.

TABLE 8

Extrinsic and intrinsic framework for studying heterologous gene products.

| Dually-expressed gene | Coupling type | Cellular dependency | Molecular "Framework" |
|---|---|---|---|
| Biopolymer X or $X_{mutant}$ (identical) | ligand-dependent (extrinsic) | dependent | X couples normally to cellular effectors (e.g. signal transduction gene) |
| Biopolymer X or $X_{mutant}$ (identical) | ligand-dependent (extrinsic) | independent | X inducibly active and bypasses cellular effectors (e.g. ion channel) |
| Biopolymer X or $X_{mutant}$ (identical) | ligand-independent (intrinsic) | dependent | X active and requires cellular effectors (e.g. kinase or oncogene) |
| Biopolymer X or $X_{mutant}$ (identical) | ligand-independent (intrinsic) | independent | X active and bypasses cellular effectors (e.g. mutant ion channel) |

Experimental Considerations

Transgenic animals dually transformed with identical heterologous biopolymer can exhibit immobility, even at low copy number transformation. Expressing identical receptors in each class of sensory cell allows 'calibration' of the sensory response. In one embodiment, expression levels of Receptor X can be calibrated to produce an organism strain that is effectively 'neutral' in response to a known chemical, Ligand X (see FIG. 2). For example, transcriptional promoters can be chosen that direct appropriate expression of a given biopolymer (e.g. proteinaceous receptor) in each class of sensory cell in a paired set (e.g. chemorepulsive and chemoattractive). Heterologous expression techniques, e.g. multimerized promoters and/or stabilizing untranslated gene segments (UTRs), and/or overexpression from high copy transgenic array, can also be employed to organismally 'titrate' biopolymer levels.

When appropriately 'calibrated', instead of migrating normally towards the normally chemoattractive Ligand X, the organism remains immobile or nearly immobile, by virtue of receiving opposing inputs from both chemoattractive and chemorepulsive cells (or other paired set or sets of neurons 'wired' in said organism to produce forward-directed and backward-directed movement). Strains are isolated with appropriate responsiveness. In this embodiment, unknown chemicals are tested to determine if their application recapitulates the same immobile sensory response, indicating that the unknown chemical interacts with researcher-defined (pre-determined) biopolymers ("drug discovery"). These embodiments elucidate whether known or unknown factors such as small molecules interact with (e.g. bind) known biopolymers.

In some embodiments, immobility is not observed but rapid cycling and/or oscillating of a mobility response is observed instead. This cycling and/or oscillating response is easily observed compared to non-responding organisms. Known and/or unknown chemicals can be tested to observe immobility response, oscillating response, and/or cycling response.

In embodiments where identical biopolymers are expressed in both chemoattractive and chemorepulsive cells, chemical activation of biopolymer is generally indistinguishable from chemical inhibition of biopolymer, as ascertained by the mobility assays described herein. In embodiments where identical biopolymers are expressed in both chemoattractive and chemorepulsive cells, chemical activation/inhibition of biopolymer is generally indistinguishable from chemical-induced toxicity and/or degeneration, as ascertained by the mobility assays described herein. Methods described in Section B below, and additional sections described herein, enable a novel method of site-specific small molecule/biopolymer (structural) analysis, a novel method of drug discovery, and a novel method of drug refinement.

In some embodiments levels of identical biopolymers and/or drug targets and/or proteinaceous components in each mediator of oppositely-directed or nearly oppositely-directed movement are manipulated for any one of a variety of purposes, including a. increasing assay sensitivity (e.g. threshold modulation—increasing/reducing heterologous expression to suppress undesired movement), and/or b. increasing assay sensitivity (e.g. gain modulation—increasing/reducing heterologous expression to increase response to desired signal), and/or c. titrate relative levels of biopolymer in oppositely-directed or nearly oppositely-directed mediators of movement relative to each other (e.g. 'fine tuning' mobility).

In some embodiments, levels of identical biopolymers and/or drug targets and/or proteinaceous components in each mediator of oppositely-directed or nearly oppositely-directed movement are manipulated independently of each other in order to 1. decrease 'false positive' responsiveness (e.g. increasing expression in chemorepulsive cells to reduce responsiveness to environmental chemoattractants), and/or 2. increase assay sensitivity (e.g. increasing expression in chemoattractive cells to increase responsiveness to applied agonists and/or antagonists). In some embodiments, levels of identical biopolymers and/or drug targets and/or proteinaceous components in each mediator are modulated to increase 'dynamic range' of an assay.

In some embodiments, heterologous expression in one class of mediator (one class of a paired set) is reduced to zero or nearly zero, or obviated entirely, to effect the desired responsiveness. In some embodiments heterologous expression in one class of mediator (one class of a paired set) is titrated relative to endogenous activity of known or unknown components to effect the desired responsiveness. In some embodiments titrating heterologous expression relative to endogenous components, expression in one class of mediator (one class of a paired set) is reduced to zero or nearly zero to effect the desired responsiveness. In some embodiments only one class of mediator is manipulated to effect an assay by the methods described herein (e.g. either forward-directed mediator or backward-directed mediator, but not both).

In embodiments described herein, mediators are paired to direct movement in two detectably different manners, paired mediators directing forward and backward movement being an excellent mode of disclosed embodiments. In an alternative embodiment, one mediator directs forward movement and a second mediator directs side-to-side movement (i.e. foraging behavior). In an alternative embodiment, one mediator directs forward movement and a second mediator directs upward vertical movement (i.e. hopping or flying behavior). In an alternative embodiment, one mediator directs forward movement and a second mediator directs downward vertical movement (i.e. burrowing or cessation-of-flying behavior). In an alternative embodiment, one mediator directs forward movement and a second mediator directs circular movement (i.e. coiling behavior). In embodiments described, co-activation of mediators described enables observation of a 'composite' behavior, such as immobility observed by co-activation of forward and reverse mediators.

In an alternative embodiment, one mediator that directs forward movement and a second mediator directs immobility (e.g. by pan-neural expression). This embodiment can be implemented in limited assays where both mediators are not co-activated (immobility being caused by two different mechanisms and thus indistinguishable).

In some embodiments, identical biopolymers and/or drug targets and/or proteinaceous components are expressed in mediators of oppositely-directed (and/or other detectably different manners) as described herein. Mediators of movement in this embodiment specifically includes cells (e.g. neurons) directly responsible for transducing chemosensation (i.e. chemotaxis) such chemosensory neurons, interneurons (if any), motor neurons, and muscle involved in organism movement (e.g. direct mediation of movement via a known circuit). In this embodiment, the organism is immobile or nearly immobile by virtue of heterologous expression of a biopolymer under study (i.e. heterologous repression of motility). For example, a mutated ion channel expressed in both mediators (forward and backward motor neurons) causes immobility by virtue of being constitutively active in both mediators (e.g. hyper-polarizing and/or depolarizing signaling neurons).

Alternatively, pairs of neurons could constituitively immobilize the organism by virtue of neurotransmitter and/or neuropeptide release in mediators (e.g. cells) directing opposite or distinguishable movement. Small molecule chemical compound(s) can be assayed to determine if activity of one or more such compounds results in derepression of immobility. Small molecules (chemical compounds) may be tested in an assay in numerous geometric configurations, as described herein, including placing a small molecule (chemical compound) in a ring around test organisms so manipulated; in the assay described test organisms will become immobilized if surrounded by sufficiently concentrated chemical(s) with a desired activity against a biopolymer under investigation.

In an alternative embodiment, identical biopolymers and/or drug targets and/or proteinaceous components are expressed in indirect mediators of oppositely-directed (and/or other detectably different manners) as described herein. In this embodiment mediators include cells that modulate neurons responsible for chemosensation and/or motor activity, e.g. by synapsing onto neurons involved in organism movement (i.e. indirect mediators of movement). Organisms, biopolymers, and small molecules can be analyzed as described.

B. Single Biopolymer: Mutated Expression

Structural data for small molecule binding interactions can be obtained by expressing nearly identical biopolymers in each class of sensory cell, such as expressing an unmutated biopolymer in chemorepulsive cells while simultaneously expressing a mutated version of the same biopolymer (e.g containing a point mutation) in chemoattractive cells. This method enables mapping of ion and/or chemical and/or small molecule (e.g. non-covalent) interactions onto biopolymer surfaces at the atomic level (i.e. "mutated push-me-pull-you" embodiment). Because the manipulated organism has been designed to be exquisitely sensitive to differential binding of ligand by directing movement in opposite directions (and/or other detectably different manners), motility will be detected for exceptionally small changes in binding affinity due to user-defined (pre-determined sites of) mutagenesis. This method of "heterozygous differentiation" can be used for isolating novel therapeutic compounds (e.g. drug discovery), or for improving pre-existing therapeutic compounds.

In the example given, decrease in activator (agonist) Ligand X binding affinity to Receptor X' (mutated) in cells directing chemoattraction results in a manipulated organism that is repelled by Ligand X, instead of remaining immobilized as in control strain expressing Receptor X identically in both chemoattractive and chemorepulsive cells. "Mutated Receptor X" is referred to herein as Receptor X'. Increase in activator (agonist) Ligand X binding affinity to Receptor X' (mutated) in cells directing chemoattraction results in a manipulated organism that is attracted to Ligand X, instead of remaining immobilized as in control strain expressing Receptor X in both chemoattractive and chemorepulsive cells. By this logic, site-specific agonists and antagonists can be readily identified and differentiated.

For an opposite class of small molecules, small molecule inhibitors, decrease in inhibitor (antagonist) Ligand X binding affinity to Receptor X' (mutated) in cells directing chemoattraction results in a manipulated organism that is attracted by Ligand X, instead of remaining immobilized as in control strain expressing Receptor X identically in both chemoattractive and chemorepulsive cells. By this logic, assays are designed that can readily identify and differentiate site-specific agonists and antagonists. An introdcutory tabel is given below (Table 9).

TABLE 9

Intrinsically and extrinsically coupled 'heterozygous' test organisms.

| Alleles expressed | Coupling type | Are animals mobile | Oriented movement in gradient of small molecule "D"? |
|---|---|---|---|
| Biopolymer X / Biopolymer X$_{mutant}$ | ligand-independent (intrinsic) | Mobile animals have mutation that abolishes, activates or uncouples activity via mutational site | If YES compared to untransformed strain then test strain has identified drug that acts directly or indirectly via mutational site on either of the two X alleles |

TABLE 9-continued

Intrinsically and extrinsically coupled 'heterozygous' test organisms.

| Alleles expressed | Coupling type | Are animals mobile | Oriented movement in gradient of small molecule "D"? |
|---|---|---|---|
| Biopolymer $X$ / Biopolymer $X_{mutant}$ | ligand-dependent (extrinsic) | Animals mobile only in uniform field of ligand compared to zero ligand control have mutation that abolishes, activates or uncouples activity via mutational site | In uniform field of ligand if YES compared to untransformed strain, test strain has identified drug that acts directly or indirectly via mutational site on either of the two X alleles |

Heterologous genes that couple positively to the locomotory circuitry will produce the following phenotypes, from which specific structural data can be obtained (Table 10).

TABLE 10

"Loco-positive" coupled heterologous biopolymers analyzed for structure or drug binding.

| "A" allele | "R" allele | Gradient of small molecule "D"? | Structural Interpretation |
|---|---|---|---|
| "loco-pos" Biopolymer X | "loco-pos" Biopolymer $X_{mutant}$ | Moves towards gradient | Ligand "D" activates X via mutational site and/or inhibits $X_{mutant}$ via mutational site |
| "loco-pos" Biopolymer X | "loco-pos" Biopolymer $X_{mutant}$ | Moves away from gradient | Ligand "D" inhibits X via mutational site and/or activates $X_{mutant}$ via mutational site |
| "loco-pos" Biopolymer $X_{mutant}$ | "loco-pos" Biopolymer X | Moves towards gradient | Ligand "D" activates $X_{mutant}$ via mutational site and/or inhibits X via mutational site |
| "loco-pos" Biopolymer $X_{mutant}$ | "loco-pos" Biopolymer X | Moves away from gradient | Ligand "D" inhibits $X_{mutant}$ via mutational site and/or activates X via mutational site |

Table 11 show negatively coupled heterologous biopolymers and interpretation.

TABLE 11

"Loco-negative" coupled heterologous biopolymers analyzed for structure or drug binding.

| "A" allele | "R" allele | Gradient of small molecule "D"? | Structural Interpretation |
|---|---|---|---|
| "loco-neg" Biopolymer X | "loco-neg" Biopolymer $X_{mutant}$ | Moves towards gradient | Ligand "D" inhibits X via mutational site and/or activates $X_{mutant}$ via mutational site |
| "loco-neg" Biopolymer X | "loco-neg" Biopolymer $X_{mutant}$ | Moves away from gradient | Ligand "D" activates X via mutational site and/or inhibits $X_{mutant}$ via mutational site |
| "loco-neg" Biopolymer $X_{mutant}$ | "loco-neg" Biopolymer X | Moves towards gradient | Ligand "D" inhibits $X_{mutant}$ via mutational site and/or activates X via mutational site |
| "loco-neg" Biopolymer $X_{mutant}$ | "loco-neg" Biopolymer X | Moves away from gradient | Ligand "D" activates $X_{mutant}$ via mutational site and/or inhibits X via mutational site |

Using methods known in the art (e.g. alanine scanning mutagenesis), precise atomic-level data can be obtained indicating decreases and/or increases in small molecule binding affinity. Such implementation has utility for increasing knowledge of specific chemical/protein interactions, such as hydrogen bonding and hydrophobic interactions, as required in rational drug design. Such implementation has utility for selecting improved versions of known pharmacologic agents. Such implementation has utility for obtaining allele-specific pharmacologic compounds (e.g. a goal of pharmacogenomics). These embodiments elucidate where known factors bind on known biopolymers, and if the binding observed is agonistic or antagonistic (see below).

In a specific embodiment, expression levels of Receptor X can be calibrated to produce an organism strain that is effectively 'neutral' in response to a known chemical, Ligand X, as described. The strain can then be mutagenized and/or recreated to produce variant strains, e.g. strains with point mutations (e.g. single amino acid changes) in the chemoreceptor (Receptor X) species. Receptor X' may be introduced and expressed, for example, only in chemorepulsive cells. Challenging the organism with Ligand X will ascertain whether mutations made to Receptor X (Receptor X') in chemorepulsive cells have identified sites in Receptor X responsible for binding Ligand X, or sites in Receptor X that allosterically affect binding of Ligand X. In the embodiment described, organisms containing mutations that directly or indirectly abolish binding of Ligand X will demonstrate alleviation of immobility.

In the embodiment described (Receptor X expressed chemoattractive cell(s) "A" while simultaneously expressing Receptor X' in chemorepulsive cell(s) "R"), if the chemical compound Ligand X activates Receptor X, but not mutated Receptor X', organisms will migrate towards a source of Ligand X. If the chemical compound inhibits Receptor X, but not mutated Receptor X', organisms will migrate away from a source of Ligand X. Both the speed of migration and the extent (distance) of migration can be scored, relative to chemical concentration. Repeating this mutagenic analysis for other point mutations enables precise, atomic level mapping of small molecule binding sites to researcher-defined (pre-determined) biopolymers such as proteinaceous receptors, proteinaceous components of the signal transduction apparatus, and RNAs.

In embodiments of this class, mutagenized biopolymers are expressed in one class of the paired mediators (e.g. either forward or backward mediators). In some embodiments, mutagenesis is employed to produce deletions, insertions, block changes, randomized subunits, truncations, etc. Mutations can be small, such as a single amino acid side chain, or a single base pair. Mutations can be very large, such as a deletions of a structural domain of a large protein.

In some embodiments, mutagenized biopolymer(s) are utilized to discover novel therapeutics (small molecules, chemical compounds, etc.). In some embodiments, mutagenized biopolymer(s) are user-defined to discover novel allele-specific therapeutics, by incorporating known allelic variants into the assay described (in one class of the paired mediators, e.g. either forward or backward mediators).

In some embodiments, mutagenized biopolymer(s) are user-defined to discover novel site-specific therapeutics. Site and extent of mutagenesis can be user-defined (pre-determined) to obviate a common site of drug binding (e.g. a charged or hydrophobic site). By mutating known sites of drug binding (in one class of the paired mediators, e.g. either forward or backward mediators), novel site-specific chemical compounds are selected that differentially activate/inhibit the nearly-identical biopolymers expressed as described. Chemicals recovered will have differential interaction (e.g. binding strength) between the mutated and un-mutated site on biopolymer.

In embodiments where mutagenized biopolymer(s) are user-defined to discover novel site-specific therapeutics, known therapeutic compounds are introduced into the assay to increase information content and/or specificity of the assay. For example, when a known "wild-type" biopolymer is expressed in a chemorepulsive cell, and and the same mutated biopolymer is expressed in a chemoattractive cell, chemical compounds that cause oriented migration (mobility) of organisms towards a source of chemical are either compounds that a) site-specifically activate mutated biopolymer (agonist) or b) site-specifically inhibit wild-type biopolymer (antagonist). Addition of known therapeutic agents that are known activators/inhibitors (agonist/antagonist) of wild-type biopolymer assists in differentiating compounds of these two classes. For example, addition of a known site-specific wild-type biopolymer inhibitor (antagonist) acts to competitively decrease the rate of mobility for chemicals that inhibit wild-type biopolymer at the same site, but noncompetitively decreases the rate of mobility for chemicals that act on the mutated biopolymer at other than the same site (the cognate site having been mutated). Competitive inhibition and non-competitive inhibition are determined by chemical titration methods known in the art.

In some embodiments, mutagenized biopolymer(s) and pre-determined pharmacological agents are utilized to discover novel site-specific therapeutics (small molecules, chemical compounds, etc.) of either or both chemical classes, as described. Organisms expressing identical and dually-mutated biopolymer are used to assist in determining site of action. For example, a chemical compound isolated in a "heterozygous" screen is demonstrated to cause immobility in either a dually wild-type strain, or a dually (identically) mutated strain, but not both strains.

In the fourth instance, a Biopolymer Y is specifically inserted into Biopolymers X, and the dually chimeric Biopolymers X/Y are expressed in paired mediators of movement, one in each mediator, as described. In one embodiment, Biopolymer Y may be utilized to act as a Ligand Response Element. In one embodiment, Biopolymers X is a known mediator of opposite or nearly-opposite movement, and expressed in the appropriate cell or cells. Insertion of Biopolymer Y (or portions thereof) enable rapid implementation of assays as described (e.g. assays for drug discovery, assays for structural mapping, assays for drug refinement). Biopolymers mutated as described (i.e. by insertion of ectopic sequence) can themselves be mutated in subsequent rounds of mutagenesis, individually as in these embodiments (heterozygous analysis), or simultaneously (see Primary Embodiment 3).

2. Differential Biopolymer Expression.

2A. Differential Modulation by Small Molecule(s)

In a primary embodiment, sensory cells are manipulated to express different biopolymers in each class of sensory cell (chemoattractive and chemorepulsive). The organism is challenged with known or unknown small molecules (e.g. chemical compounds as may be used for pharmacological intervention). Small molecules that elicit desired responses (e.g. chemoattraction to Receptor X expressed in chemoattractive cell "A" despite presence of Receptor Y expressed in chemorepulsive cell "R"). Such implementation has utility for obtaining small molecule chemical compounds that are bioactive, but have reduced Receptor Y-mediated toxicity, as ascertained by reduced chemorepulsive behavior mediated through Receptor Y). Such implementation also has utility for recovering small molecule chemical compounds that are bioactive against biopolymers (e.g. proteinaceous receptors) normally expressed at low levels relative to other biopolymers (e.g. proteinaceous receptors), as exemplified by Receptor Y.

In one embodiment, the materials and methods described herein are used to identify variant compounds related to a known compound, Ligand X, that interacts with a known receptor, Receptor X, but with improved pharmacological properties. In one exemplary embodiment, a known compound Ligand X has a toxic side effect mediated by another receptor, Receptor Y. To identify factors interacting with Receptor X while alleviating toxicity mediated by Receptor Y, an organismal strain is produced that expresses the natural or desired chemoreceptor interaction, Receptor X, in chemoattractive cells, while also expressing Receptor Y in chemorepulsive cells. An assay improvement is to use a strain of organism that results in organismal 'coiling' when moving backwards, not a linear backward movement. Motility of the organism strain described is calibrated alone or in the presence of Ligand X. For example, expression of Receptor Y in chemorepulsive cells is manipulated to such a level that the organism strain described is-immobile or nearly immobile in the presence of Ligand X, despite the presence of Receptor X in chemoattractive cells. Once calibrated, variant and/or novel chemical compounds can be tested to determine if chemoattractive migration is elicited. If chemoattractive migration is elicited, one or more variant and/or novel chemical compounds isolated (i.e. Ligand X') represent novel therapeutic agent or agents, or a novel use for known therapeutic agent or agents. Said agent(s) have the important pharmacological property of eliciting a desired biological response in the presence of a known inhibitory biopolymer species, Receptor Y. Various 'control' experiments utilizing strains expressing Receptor X but not Receptor Y, or expressing Receptor Y but not Receptor X, are performed to derive motility information for receptors expressed individually, to ensure that motility differences observed are due to the absence/presence of the second receptor species within the same organism. Agent(s) identified are novel, useful, and non-obvious chemical (i.e.

pharmacologic) agent(s), as well as an improvement over prior art, Ligand X (i.e. drug refinement).

In one exemplary embodiment, a known receptor Receptor X is studied for its potential use as a therapeutic target. In one scenario, preliminary studies suggest that Receptor X agonists (activators) may be potent therapeutic agents. However, studies of Receptor X are hampered by co-expression of Receptor X with Receptor Y in the same cell and/or tissue and/or organ and/or organism. The presence of Receptor Y (possibly expressed at high levels) may interfere with cellular and/or cell free assays designed to isolate novel pharmacological compounds that interact specifically with Receptor X. To identify factors interacting with Receptor X while alleviating assay interference by Receptor Y, a differential biopolymer embodiment is implemented. An organismal strain is produced that expresses Receptor Y in chemorepulsive cells, while also expressing the natural or desired chemoreceptor interaction, Receptor X, in chemoattractive cells. Motility of the organism strain described may be calibrated alone or in the presence of Ligand Y, a compound known to activate Receptor Y. For example, expression of Receptor Y in chemorepulsive cells may be manipulated to such a level that the organism strain described is immobile or nearly immobile in the presence of Ligand Y, despite the presence of Receptor X in chemoattractive cells.

At this point, known and/or unknown variant and/or novel chemical compounds can be tested to determine if chemoattractive migration is elicited in the presence and/or absence of Ligand Y. If chemoattractive migration is elicited, the variant and/or novel chemical compounds represents a novel therapeutic agent, or a novel use for a known therapeutic agent. Chemical agent(s) recovered using the methods described herein are specifically targeted against Receptor X, and are capable of eliciting a desired biological response in the presence of a known inhibitory cellular and/or organismal species, represented by Receptor Y.

In some embodiments, a particular member of a gene family, Receptor X, may be expressed in an organism within a target tissue, however similar members of the same family (e.g. Receptor Y) are expressed in non-target tissue that causes deleterious effect when modulated by known therapeutics. Organisms and/or biopolymers expressed as described herein are employed in a strategy to identify novel ("second generation") therapeutics that modulate Receptor X but not Receptor Y.

In some embodiments, organisms expressing biopolymers as described herein are employed in a strategy to differentially identify human therapeutics and biocontrol agents, or both. For example, Receptor X may represent a human receptor while Receptor Y may represent an orthologous gene from a human symbiont and/or pathogen. Organisms expressing biopolymers as described herein are employed in a strategy to identify therapeutic compounds that modulate the human gene (e.g. activating cellular growth and/or differentiation) while having no growth-promoting effect on distally-related (i.e. orthologous) biopolymers present in human symbionts and/or pathogens. In some embodiments, organisms expressing biopolymers as described herein are employed in a strategy to identify therapeutic compounds that eradicate human pathogens without affecting normal human processes mediated by distally-related (i.e. orthologous) human biopolymers.

Various 'control' experiments utilizing strains expressing Receptor X but not Receptor Y, or expressing Receptor Y but not Receptor X, are performed to derive motility information for receptors expressed individually, to ensure that motility differences observed are due to the absence/presence of the second receptor species within the same organism. Novel pharmacological agent(s) identified can be viewed as both a novel, useful, and non-obvious chemical agent(s), as well as an improvement over prior agents such as Ligand X, or other agents identified in the presence of Receptor Y (i.e. drug refinement).

2A. Identical Modulation by Small Molecule(s)

In some embodiments, organisms modified as described are used to detect and/or identify small molecules (i.e. chemical compounds and/or novel therapeutic agents) that interact with both Receptor X and/or biopolymer X expressed in chemoattractive cell(s) "A" and Receptor Y and/or biopolymer Y expressed in chemorepulsive cell(s) "R", by induced immobility as described herein. Organisms and/or biopolymers expressed as described can be used to identify sites on two dissimilar biopolymers, Receptors X and Y, that have common structural elements, as detected by one or more small molecules (e.g. therapeutic compounds).

TABLE 12

Test organisms and interpretation for two positively coupled heterologous biopolymers (top) and two negatively coupled biopolymers (bottom).

| "A" allele | "R" allele | Gradient of small molecule "D"? | Structural Interpretation |
| --- | --- | --- | --- |
| "loco-pos" Biopolymer X | "loco-pos" Biopolymer Y | Moves towards gradient | Ligand "D" activates X and/or inhibits Y |
| "loco-pos" Biopolymer X | "loco-pos" Biopolymer Y | Moves away from gradient | Ligand "D" inhibits X and/or activates Y |
| "loco-pos" Biopolymer Y | "loco-pos" Biopolymer X | Moves towards gradient | Ligand "D" activates Y and/or inhibits X |
| "loco-pos" Biopolymer Y | "loco-pos" Biopolymer X | Moves away from gradient | Ligand "D" inhibits Y and/or activates X |
| "loco-neg" Biopolymer X | "loco-neg" Biopolymer Y | Moves towards gradient | Ligand "D" inhibits X and/or activates Y |
| "loco-neg" Biopolymer X | "loco-neg" Biopolymer Y | Moves away from gradient | Ligand "D" activates X and/or inhibits Y |
| "loco-neg" Biopolymer Y | "loco-neg" Biopolymer X | Moves towards gradient | Ligand "D" inhibits Y and/or activates X |
| "loco-neg" Biopolymer Y | "loco-neg" Biopolymer X | Moves away from gradient | Ligand "D" activates Y and/or inhibits X |

3. Dual Mutagenesis and/or Recombined Expression.

In embodiments of this class, mutagenized biopolymers are expressed in both paired mediators. In some embodiments, a single biopolymer is mutagenized and/or recombined and mutagenized progeny expressed in paired mediators (one mutated progeny in each mediator). In some embodiments two different biopolymers are mutagenized and/or recombined and expressed in paired mediators (one mutated progeny in each mediator).

3A. Dual Mutagenesis Expression

In a primary embodiment, sensory cells are manipulated to express mutated biopolymers in each class of sensory cell (i.e. mobility mediator). In the first instance, an identical biopolymer is mutated to produce identically mutated biopolymers, which are expressed in each class of sensory cell (i.e. mobility mediator). Novel therapeutic compounds ("drug discovery") can be selected by inducing an immobility response. Site and extent of mutagenesis can be user-defined (pre-determined) to obviate a common site of drug binding (e.g. a charged or hydrophobic site). The class of novel therapeutic compounds recovered will be novel in that a site of previous chemical interaction has been ablated, thus any novel compounds isolated must interact at different sites (or at the newlymutated site) on the biopolymer surface.

In some embodiments, sensory cells are manipulated to express differentially mutated biopolymers in each class of sensory cell (i.e. mobility mediator). For example, a biopolymer encoded by gene X can be mutated and expressed such that gene X mutant 1 is expressed in chemoattractive cell "A", while gene X mutant 2 is expressed in chemorepulsive cell "R". User-defined organisms as described are useful for mapping the sites of known chemical interactions, such as binding sites for known therapeutic agents, in implementation of a strategy for isolating second-generation therapeutic agents.

In some embodiments, a single biopolymer is mutated, and identically mutated biopolymers are expressed, one in each class of a paired set of mobility mediator (e.g. chemoattractive/repulsive neuron set). For example, a receptor may be truncated (i.e. deleted) at the amino terminus, identical amino-deleted constructs heterologously-expressed in paired sets of chemosensory neurons (e.g. chemoattractive and chemorepulsive neurons), and mobility assayed as described, in the presence and/or absence of small molecule(s). Changes in responsiveness are attributable to the deleted region, when compared with control strains expressing full length receptor in paired sets of mediators.

In some embodiments, a single biopolymer is mutated two different ways, and differentially mutated biopolymers are expressed, one in each class of a paired set of mobility mediator (e.g. chemo-attractive/repulsive neuron set). For example, a receptor may be truncated (i.e. deleted) at the carboxyl terminus to generate two different-sized truncations, differentially carboxyl-deleted constructs are heterologously-expressed in paired sets of chemosensory neurons (e.g. chemoattractive and chemorepulsive neurons), one deletion size expressed in each class of cell (either chemoattractive or chemorepulsive). Mobility is assayed as described, in the presence and/or absence of small molecule(s). Changes in responsiveness are attributable to the differentially deleted region, when compared with control strain(s) expressing identical deletions in paired sets of mobility mediators (e.g. neurons expressing identical constructs with a short carboxyl truncation, or neurons expressing identical constructs with a long carboxyl truncation).

3B. Recombined Expression

In a primary embodiment, sensory cells are manipulated to express recombined (i.e. chimeric) biopolymers (e.g. proteinaceous receptors) in each class of sensory cell. Embodiments of this category exchange heterologously-expressed material between paired set(s) of mediators (e.g. neurons).

For example, a single biopolymer is heterologously-expressed in both classes of mediators, but compared to prior embodiments, in this embodiment genetic material is exchanged between the two expression constructs. For example, one construct is deleted for a putative ligand-binding domain, while the other construct is duplicated for the same putative ligand-binding domain. Methods for producing biopolymers with exchanged genetic material are known in the art (e.g. unequal crossing over). Exchanges of genetic material in this manner rapidly identify sites of ligand binding by the assays described herein. Assays include ascertaining bioactivity by chemo-attraction/repulsion in the same manner as described. Such implementation has utility in mapping the site(s) of small molecule (e.g. drug) binding to specific linear segments of biomolecules (e.g. amino acid sequences).

In some embodiments, two different biopolymers are recombined and/or mutated. For example, chimeric receptor X(1–100aa)/Y(10–200aa) is expressed in chemoattractive Cell A, while reciprocal chimeric receptor Y(1–100aa)/X (101–200aa) is expressed in chemorepulsive Cell B. Bioactivity is ascertained by chemo-attraction/repulsion in the same manner as described. Such implementation has utility in mapping the site(s) of small molecule (e.g. drug) binding to specific linear segments of biomolecules (e.g. amino acid sequences).

In some embodiments, mutagenesis is employed to produce deletions, insertions, block changes, randomized subunits, truncations, etc. Mutations can be small, such as a single amino acid side chain, or a single base pair. Mutations can be very large, such as a structural domain of a large protein.

In a specific embodiment, a small molecule (chemical) interacts with a receptor. Analysis may be performed as in Primary Embodiment 1 to localize a site or sites of interaction between the small molecule Ligand X, and the receptor, Receptor X. This region (sub-segment of Receptor X) is generally referred to as Ligand X Response Element. Once identified, the sub-segment of Receptor X responsible for mediating interaction with chemical (Ligand X Response Element) can be incorporated into a chimeric biopolymer.

In the first instance, a receptor known to be non-responsive to chemical, Receptor Y, is made responsive to chemical, Ligand X, by the creation of a chimeric receptor, Receptor X/Y. Assays are performed as in Primary Embodiment 1 to demonstrate that the chimeric receptor now responds appropriately to chemical, by induced motility (or induced immobility).

An example of such implementation is chimeragenesis or insertion of a known Ligand X Response Element, such as segments from a known protein that bind antibiotics (e.g. tetracycline, etc.). Use of the methods described herein enable rapid, functional analysis of biopolymers, such as receptors, industrial catalysts, and biopharmaceuticals. These biopolymers can be made functionally responsive to small molecule ligands (e.g. therapeutics, antibiotics, and cellular cofactors), by the methods described herein.

In the second instance, regions of Receptor Y capable of functionally accepting Ligand X Response Element are mapped onto Receptor Y primary sequence. Chimeric receptors are generated incorporating Ligand X Response Element at different locations within Receptor Y, defining regions of Receptor Y that are capable of transducing signals from Ligand X Response Element.

An example of such an implementation is comparing two related receptors that respond differently to applied agonists and/or antagonists, such as Ligand X. Regions responsible for responsiveness can be swapped by making reciprocal chimeric receptors. Induced motility in recombined receptors compared to 'balanced' immobility in un-recombined receptors can ascertain the location of putative Ligand X Response Element(s) within one of the two recombined receptors.

In the third instance, two receptors, Receptor X and Receptor Y, each respond very poorly to an individual chemical species, Ligand Z. Chimeric receptors are generated between Receptor X and Receptor Y to determine if responsiveness to Ligand Z can be improved (i.e. synergistic response in a novel single element and/or additive response of multiple elements). Chimeric receptors are tested in motility assays where reciprocal chimeric receptors are heterologously expressed in chemoattractive and chemorepulsive cells, to determine if responsiveness to chemical Ligand Z is substantially improved. Ligand binding regions can be identified and localized in this manner, and additionally refined using mutagenesis methods (single biopolymer mutated expression) described herein.

In the fourth instance, a Biopolymer Z is specifically inserted into two different Biopolymers X and Y, and the dually chimeric Biopolymers X/Z and Y/Z are expressed in paired mediators of movement, one in each mediator, as described. In one embodiment, Biopolymer Z may be utilized to act as a Ligand Response Element. In one embodiment, Biopolymers X and Y are known mediators of opposite movement or mediators directing movement in detectably different manners: insertion of Biopolymer Z (or portions thereof) enable rapid implementation of assays as described (e.g. assays for drug discovery, assays for structural mapping, assays for drug refinement).

Biopolymers mutated as described (i.e. by insertion of ectopic sequence) can themselves be mutated in subsequent rounds of mutagenesis, individually (heterozygous analysis; Primary Embodiment 1), or simultaneously as in these embodiments.

II. Definitions

Unless otherwise defined, all technical and scientific terms used herein have the same meaning as commonly understood by one of ordinary skill in the art to which the presently disclosed subject matter pertains. For clarity of the present specification, certain definitions are presented herein below.

Following long-standing patent law convention, the terms "a" and "an" mean "one or more" when used in this application, including in the claims.

As used herein, the term "about," when referring to a value or to an amount of mass, weight, time, volume, concentration or percentage is meant to encompass variations of ±20% or ±10%, in another example ±5%, in another example ±1%, and in still another example ±0.1% from the specified amount, as such variations are appropriate to practice the presently disclosed subject matter. Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that can vary depending upon the desired properties sought to be obtained by the presently disclosed subject matter.

As used herein, the terms "amino acid" and "amino acid residue" are used interchangeably and refer to any of the twenty naturally occurring amino acids, as well as analogs, derivatives, and congeners thereof; amino acid analogs having variant side chains; and all stereoisomers of any of any of the foregoing. Thus, the term "amino acid" is intended to embrace all molecules, whether natural or synthetic, which include both an amino functionality and an acid functionality and capable of being included in a polymer of naturally occurring amino acids.

An amino acid may be formed upon chemical digestion (hydrolysis) of a polypeptide at its peptide linkages. The amino acid residues described herein are in some embodiments in the "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature abbreviations for amino acid residues are shown in tabular form presented hereinabove.

It is noted that all amino acid residue sequences represented herein by formulae have a left-to-right orientation in the conventional direction of amino terminus to carboxy terminus. In addition, the phrases "amino acid" and "amino acid residue" are broadly defined to include modified and unusual amino acids.

Furthermore, it is noted that a dash at the beginning or end of an amino acid residue sequence indicates a peptide bond to a further sequence of one or more amino acid residues or a covalent bond to an amino-terminal group such as $NH_2$ or acetyl or to a carboxy-terminal group such as COOH.

As used herein, the terms "associated with" and "operatively linked" refer to two nucleic acid sequences that are related physically or functionally. For example, a promoter or regulatory DNA sequence is said to be "associated with" a DNA sequence that encodes an RNA or a polypeptide if the two sequences are operatively linked, or situated such that the regulator DNA sequence will affect the expression level of the coding or structural DNA sequence.

As used herein, the terms "coding sequence" and "open reading frame" (ORF) are used interchangeably and refer to a nucleic acid sequence that is transcribed into RNA such as mRNA, rRNA, tRNA, snRNA, sense RNA, or antisense RNA. In some embodiments, the RNA is then translated in vivo or in vitro to produce a polypeptide. In some embodiments the RNA is maintained structurally in the cell (so-called structural RNAs). Classes of structural RNAs include but are not limited to rRNA, tRNA, snRNA, miRNA, siRNA, and XIST RNA.

As used herein, the term "complementary" refers to two nucleotide sequences that comprise anti-parallel nucleotide sequences capable of pairing with one another upon formation of hydrogen bonds between the complementary base residues in the anti-parallel nucleotide sequences. As is known in the art, the nucleic acid sequences of two complementary strands are the reverse complement of each other when each is viewed in the 5' to 3' direction.

As is also known in the art, two sequences that hybridize to each other under a given set of conditions do not necessarily have to be 100% fully complementary. As used herein, the terms "fully complementary" and "100% complementary" refer to sequences for which the complementary regions are 100% in Watson-Crick base-pairing; i.e., that no mismatches occur within the complementary regions. However, as is often the case with recombinant molecules (for example, cDNAs) that are cloned into cloning vectors, certain of these molecules can have non-complementary overhangs on either the 5' or 3' ends that result from the cloning event. In such a situation, it is understood that the region of 100% or full complementarity excludes any sequences that are added to the recombinant molecule (typically at the ends) solely as a result of, or to facilitate, the cloning event. Such sequences are, for example, polylinker sequences, linkers with restriction enzyme recognition sites, etc.

As used herein, the term "expression cassette" refers to a nucleic acid molecule capable of directing expression of a particular nucleotide sequence in an appropriate host cell, comprising a promoter operatively linked to the nucleotide sequence of interest which is operatively linked to termination signals. It also typically comprises sequences required for proper translation of the nucleotide sequence. The coding region usually encodes a polypeptide of interest but can also encode a functional RNA of interest, for example antisense RNA or a non-translated RNA, in the sense or antisense direction. The expression cassette comprising the nucleotide sequence of interest can be chimeric, meaning that at least one of its components is heterologous with respect to at least one of its other components. The expression cassette can also be one that is naturally occurring but has been obtained in a recombinant form useful for heterologous expression. Typically, however, the expression cassette is heterologous with respect to the host; i.e., the particular DNA sequence of the expression cassette does not occur naturally in the host cell and was introduced into the host cell or an ancestor of the host cell by a transformation event. The expression of the nucleotide sequence in the expression cassette can be under the control of a constitutive promoter or of an inducible promoter that initiates transcription only when the host cell is exposed to some particular external stimulus. In the case of a multicellular organism such as a plant, the promoter can also be specific to a particular tissue, organ, or stage of development.

As used herein, the term "expression product" usually refers to a polypeptide of interest, but can also refer to a functional RNA of interest. Functional RNAs of interest include ribozymes, miRNAs, and RNAs known to effect RNA-interference (RNAi).

The term "expression vector" as used herein refers to a DNA sequence capable of directing expression of a particular nucleotide sequence in an appropriate host cell, comprising a promoter operatively linked to the nucleotide sequence of interest which is operatively linked to transcription termination sequences. It also typically comprises sequences required for proper translation of the nucleotide sequence. The construct comprising the nucleotide sequence of interest can be chimeric. The construct can also be one that is naturally occurring but has been obtained in a recombinant form useful for heterologous expression. The nucleotide sequence of interest, including any additional sequences designed to effect proper expression of the nucleotide sequences, can also be referred to as an "expression cassette".

As used herein, the terms "fragment," "sub-sequence," and "sub-segment" refer to a sequence that comprises a subset of another sequence. When used in the context of a nucleic acid or amino acid sequence, the terms "fragment", "subsequence" and "sub-segment" are used interchangeably. A fragment of a nucleic acid sequence can be any number of nucleotides that is less than that found in another nucleic acid sequence, and thus includes, but is not limited to, the sequences of an exon or intron, a promoter, an enhancer, an origin of replication, a 5' or 3' untranslated region, a coding region, and a polypeptide binding domain. It is understood that a fragment or subsequence can also comprise less than the entirety of a nucleic acid sequence, for example, a portion of an exon or intron, promoter, enhancer, etc. Similarly, a fragment or subsequence of an amino acid sequence can be any number of residues that is less than that found in a naturally occurring polypeptide, and thus includes, but is not limited to, domains, features, repeats, etc. Also similarly, it is understood that a fragment or subsequence of an amino acid sequence need not comprise the entirety of the amino acid sequence of the domain, feature, repeat, etc. A fragment can also be a "functional fragment," in which the fragment retains a specific biological function of the nucleic acid sequence or amino acid sequence of interest. For example, a functional fragment of a transcription factor can include, but is not limited to, a DNA binding domain, a transactivating domain, or both. Similarly, a functional fragment of a receptor tyrosine kinase includes, but is not limited to a ligand binding domain, a kinase domain, an ATP binding domain, and combinations thereof.

As used herein, the term "gene" refers to a nucleic acid that encodes an RNA, for example, nucleic acid sequences including, but not limited to, structural genes encoding a polypeptide or genes encoding a structural RNA. The term "gene" also refers broadly to any segment of DNA associated with a biological function. As such, the term "gene" encompasses sequences including, but not limited to a coding sequence, a promoter region, a transcriptional regulatory sequence, a non-expressed DNA segment that is a specific recognition sequence for regulatory proteins, a non-expressed DNA segment that contributes to gene expression, a DNA segment designed to have desired parameters, or combinations thereof. A gene can be obtained by a variety of methods, including cloning from a biological sample, synthesis based on known or predicted sequence information, and recombinant derivation from one or more existing sequences.

As is understood in the art, a gene comprises a coding strand and a noncoding strand. As used herein, the terms "coding strand" and "sense strand" are used interchangeably, and refer to a nucleic acid sequence that has the same sequence of nucleotides as an mRNA from which the gene product is translated. As is also understood in the art, when the coding strand and/or sense strand is used to refer to a DNA molecule, the coding/sense strand includes thymidine residues instead of the uridine residues found in the corresponding mRNA. Additionally, when used to refer to a DNA molecule, the coding/sense strand can also include additional elements not found in the mRNA including, but not limited to promoters, enhancers, and introns. Similarly, the terms "template strand" and "antisense strand" are used interchangeably and refer to a nucleic acid sequence that is complementary to the coding/sense strand.

The term "gene expression" generally refers to the cellular processes by which a biologically active polypeptide is produced from a DNA sequence and exhibits a biological activity in a cell. As such, gene expression involves the processes of transcription and translation, but also involves post-transcriptional and post-translational processes that can influence a biological activity of a gene or gene product. These processes include, but are not limited to RNA syntheses, processing, and transport, as well as polypeptide synthesis, transport, and post-translational modification of polypeptides, either individually or in any combination of more than one. Additionally, processes that affect protein-protein interactions within the cell can also affect gene expression as defined herein.

The terms "heterologous," "recombinant," and "exogenous," when used herein to refer to a nucleic acid sequence (e.g. a DNA sequence) or a gene, generally refer to a sequence that originates from a source foreign to the particular host cell or, if from the same source, is modified from its original form. Thus, a heterologous gene in a host cell includes a gene that is endogenous to the particular host cell but has been modified through, for example, the use of site-specific mutagenesis or other recombinant techniques (for example, cloning the gene into a vector). Thus, exogenous DNA segments can be expressed to yield exogenous polypeptides. The terms also include non-naturally occurring multiple copies of a naturally occurring DNA sequence. In the specific case of tandemly duplicated nucleic acid sequences, for example within a gene, the duplication is considered to be in a "heterologous" position relative to its natural location.

The terms "heterologous gene," "heterologous DNA sequence," "heterologous nucleotide sequence," "exogenous nucleic acid molecule," or "exogenous DNA segment," as used herein, each refer to a sequence that originates from a source foreign to an intended host cell or, if from the same source, is modified from its original form. When used in context of a cell or organism, the terms refer to a DNA segment that is foreign or heterologous to the cell, or homologous to the cell but in a position or form within the host cell in which the element is not ordinarily found. Thus, a heterologous gene in a host cell includes a gene that is endogenous to the particular host cell but has been modified, for example by mutagenesis or by isolation from native transcriptional regulatory sequences. The terms also include non-naturally occurring multiple copies of a naturally occurring nucleotide sequence. Thus, the terms refer to a DNA segment that is foreign or heterologous to the cell, or homologous to the cell but in a position within the host cell nucleic acid wherein the element is not ordinarily found. When referring to a nucleic acid sequence, for example in the tandem duplication of a nucleic acid sequence, the duplication is considered to be in a "heterologous nucleotide sequence" or "heterologous DNA sequence" relative to sequence present in its natural or "homologous" position.

A "homologous" or "endogenous" nucleic acid (or amino acid) sequence is a nucleic acid (or amino acid) subsequence in its natural position within a nucleic acid sequence, gene, or expression product thereof, or naturally associated with a cell into which it is introduced. When referring to a cell, a "homologous" or "endogenous" nucleic acid (or amino acid) sequence is a nucleic acid (or amino acid) sequence in its natural position within a gene, or naturally associated with a cell into which it is introduced.

The phrase "hybridizing specifically to" refers to the binding, duplexing, or hybridizing of a molecule only to a particular nucleotide sequence under stringent conditions when that sequence is present in a complex mixture (e.g. total cellular) DNA or RNA. The phrase "hybridize(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

An "isolated" nucleic acid molecule or protein, or biologically active portion thereof, is substantially free of other cellular material, or culture medium when produced by recombinant techniques, or substantially free of chemical precursors or other chemicals when chemically synthesized. Thus, the term "isolated nucleic acid" refers to a polynucleotide of genomic, cDNA, or synthetic origin or some combination thereof, which (1) is not associated with the cell in which the "isolated nucleic acid" is found in nature, or (2) is operatively linked to a polynucleotide to which it is not linked in nature. Similarly, the term "isolated polypeptide" refers to a polypeptide, in certain embodiments prepared from recombinant DNA or RNA, or of synthetic origin, or some combination thereof, which (1) is not associated with proteins that it is normally found within nature, (2) is isolated from the cell in which it normally occurs, (3) is isolated free of other proteins from the same cellular source, (4) is expressed by a cell from a different species, or (5) does not occur in nature.

In certain embodiments, an "isolated" nucleic acid is free of sequences (e.g. protein encoding or regulatory sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of the nucleotide sequences that naturally flank the nucleic acid molecule in genomic DNA of the cell from which the nucleic acid is derived. A protein that is substantially free of cellular material includes preparations of protein or polypeptide having less than about 30%, 20%, 10%, or 5%, (by dry weight) of contaminating protein. When the protein of the presently disclosed subject matter, or biologically active portion thereof, is recombinantly produced, culture medium represents less than about 30%, 20%, 10%, or 5% (by dry weight) of chemical precursors or non-protein of interest chemicals. Thus, the term "isolated," when used in the context of an isolated DNA molecule or an isolated polypeptide, refers to a DNA molecule or polypeptide that, by the hand of man, exists apart from its native environment and is therefore not a product of nature. An isolated DNA molecule or polypeptide can exist in a purified form or can exist in a nonnative environment such as, for example, in a transgenic host cell.

The term "isolated," when used in the context of an "isolated cell," refers to a cell that has been removed from its natural environment: for example, as a part of an organ, tissue, or organism.

As used herein, the term "mutation" carries its traditional connotation and refers to a change, inherited, naturally occurring or introduced, in a nucleic acid or polypeptide sequence, and is used in its sense as generally known to those of skill in the art. For the purposes of this disclosure, "mutagenesis" is divided into two categories: base change (molecular replacement) mutagenesis and insertional/deletional mutagenesis.

As used herein, the terms "native" and "endogenous" refer to a gene that is naturally present in the genome of an untransformed cell or organism. Similarly, when used in the context of a polypeptide, a "native polypeptide" is a polypeptide that is encoded by a native gene of an untransformed cell's or organism's genome.

As used herein, the term "naturally occurring" refers to an object that is found in nature as distinct from being artificially produced by man. For example, a polypeptide or nucleotide sequence that is present in an organism (including a virus) in its natural state, which has not been intentionally modified or isolated by man in the laboratory, is naturally occurring. As such, a polypeptide or nucleotide sequence is considered "non-naturally occurring" if it is encoded by or present within a recombinant molecule, even if the amino acid or nucleic acid sequence is identical to an amino acid or nucleic acid sequence found in nature.

As used herein, the terms "nucleic acid," "nucleic acid molecule," "nucleic acid sequence," and "nucleic acid segment" refer to any of deoxyribonucleic acid (DNA), ribonucleic acid (RNA), oligonucleotides, fragments generated by the polymerase chain reaction (PCR), and fragments generated by any of ligation, scission, endonuclease action, and exonuclease action. Nucleic acids can be composed of monomers that are naturally occurring nucleotides (such as deoxyribonucleotides and ribonucleotides), or analogs of naturally occurring nucleotides (e.g. alpha-enantiomeric forms of naturally occurring nucleotides), or a combination of both. Modified nucleotides can have modifications in sugar moieties and/or in pyrimidine or purine base moieties.

Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid" also includes so-called "peptide nucleic acids", which comprise naturally occurring or modified nucleic acid bases attached to a polyamide backbone. Nucleic acids can be composed of identical chemical units, repeated chemical units, or a unique sequence of chemical units. Nucleic acids can be either single stranded or double stranded.

The term "operatively linked," when describing the relationship between two nucleic acid regions, refers to a juxtaposition wherein the regions are in a relationship permitting them to function in their intended manner. For example, a control sequence "operatively linked" to a coding sequence is ligated in such a way that expression of the coding sequence is achieved under conditions compatible with the control sequences, such as when the appropriate molecules (e.g. inducers and polymerases) are bound to the control or regulatory sequence(s). Thus, in some embodiments, the phrase "operatively linked" refers to a promoter connected to a coding sequence in such a way that the transcription of that coding sequence is controlled and regulated by that promoter. Techniques for operatively linking a promoter to a coding sequence are well known in the art; the precise orientation and location relative to a coding sequence of interest is dependent, inter alia, upon the specific nature of the promoter.

Thus, the term "operatively linked" can refer to a promoter region that is connected to a nucleotide sequence in such a way that the transcription of that nucleotide sequence is controlled and regulated by that promoter region. Similarly, a nucleotide sequence is said to be under the "transcriptional control" of a promoter to which it is operatively linked. Techniques for operatively linking a promoter region to a nucleotide sequence are known in the art. The term "operatively linked" can also refer to a transcription termination sequence or other nucleic acid that is connected to a nucleotide sequence in such a way that termination of transcription of that nucleotide sequence is controlled by that transcription termination sequence. Additionally, the term "operatively linked" can refer to an enhancer, silencer, or other nucleic acid regulatory sequence that when operatively linked to an open reading frame modulates the expression of that open reading frame, either in a positive or negative fashion.

As used herein, the term "oriented" refers to the relative direction that two or more biopolymers (e.g. nucleic acid, polypeptides) assume when placed within in the same molecule. As described herein, two or more genes or gene subsegments are considered oriented "head-to-tail" if coding sequences can be conceptually placed in a "left-to-right" direction relative to each other (e.g. initiator codon to terminator codon, N-terminus to C-terminus) in the same molecule. Similarly, an existing gene and/or protein sequence can be bisected and recombined in a natural orientation, an orientation generally understood to be "head-to-tail" or "left-to-right" orientation by those skilled in the art. "Head-to-tail" orientation is equivalent to a "direct repeat" orientation when sequences under study are substantially identical, as generally understood by those skilled in the art. Three other orientations are conceptually possible, "head-to-head", "tail-to-tail", and "tail-to-head." "Head-to-head" and "tail-to-tail" orientations are equivalent to an "inverted" and/or "inverted repeat" orientation when sequences under study are substantially identical, as generally understood by those skilled in the art. "Tail-to-head" orientation inverts the natural order of sequences, so that terminator codon or C-terminus sequences are placed in reverse order relative to initiator-codon or N-terminus sequences, should sequences be read from one end to the other. These conventions hold for any two or more nucleic acid sequences with distinguishable ends (i.e. excluding molecules with absolute dyad symmetry).

The term "phenotype" refers to the entire physical, biochemical, and physiological makeup of a cell or an organism; e.g. having any one trait or any group of traits. As such, phenotypes generally result from the expression of genes within a cell or an organism, and relate to traits that are potentially observable or assayable.

As used herein, the terms "polypeptide," "protein," and "peptide," which are used interchangeably herein, refer to a polymer and/or a biopolymer of the 20 protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. As used herein, the terms "protein," "polypeptide," and "peptide" are used interchangeably herein when referring to a gene product. The term "polypeptide" encompasses proteins of all functions, including enzymes. Thus, exemplary polypeptides include gene products, naturally occurring proteins, homologs, orthologs, paralogs, fragments, and other equivalents, variants and analogs of the foregoing.

The terms "polypeptide fragment" or "fragment," when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxyterminus of the reference polypeptide, or alternatively both. Fragments typically are at least 5, 6, 8, or 10 amino acids long, at least 14 amino acids long, at least 20, 30, 40 or 50 amino acids long, at least 75 amino acids long, or at least 100, 150, 200, 300, 500 or more amino acids long. A fragment can retain one or more of the biological activities of the reference polypeptide. In certain embodiments, a fragment can comprise a domain or feature, and optionally additional amino acids on one or both sides of the domain or feature, which additional amino acids can number from 5, 10, 15, 20, 30, 40, 50, or up to 100 or more residues. Further, fragments can include a sub-fragment of a specific region, which sub-fragment retains a function of the region from which it is derived. In some embodiments, a fragment can have immunogenic properties.

As used herein, the term "pre-polypeptide" refers to a polypeptide that comprises a transit peptide that is post-translationally removed.

As used herein, the term "primer" refers to a sequence comprising in some embodiments two or more deoxyribonucleotides or ribonucleotides, in some embodiments more than three, in some embodiments more than eight, and in some embodiments at least about 20 nucleotides of an exonic or intronic region. Such oligonucleotides are in some embodiments between ten and thirty bases in length.

The term "promoter" or "promoter region" each refers to a nucleotide sequence within a gene that is positioned 5' to a coding sequence and functions to direct transcription of the coding sequence. The promoter region comprises a transcriptional start site, and can additionally include one or more transcriptional regulatory elements. In some embodiments, a method of the presently disclosed subject matter employs a tissue-specific or cell type-specific promoter.

As used herein, the term "minimal promoter" refers to the smallest piece of a promoter, such as a TATA element, that can support any transcription. A minimal promoter typically has greatly reduced promoter activity in the absence of upstream or downstream activation. In the presence of a suitable transcription factor, a minimal promoter can function to permit transcription. As such, a "minimal promoter" is a nucleotide sequence that has the minimal elements required to enable basal level transcription to occur. Typically, minimal promoters are not necessarily complete promoters but rather can be subsequences of promoters that are capable of directing a basal level of transcription of a reporter construct in an experimental system. Minimal promoters include but are not limited to the cytomegalovirus (CMV) minimal promoter, the herpes simplex virus thymidine kinase (HSV-tk) minimal promoter, the simian virus 40 (SV40) minimal promoter, the human beta-actin minimal promoter, the human EF2 minimal promoter, the adenovirus E 1B minimal promoter, and the heat shock protein (hsp) 70 minimal promoter. Minimal promoters are often augmented with one or more transcriptional regulatory elements to influence the transcription of an operatively linked gene. For example, cell-type-specific or tissue-specific transcriptional regulatory elements can be added to minimal promoters to create recombinant promoters that direct transcription of an operatively linked nucleotide sequence in a cell-type-specific or tissue-specific manner.

Different promoters have different combinations of transcriptional regulatory elements. Whether or not a gene is expressed in a cell is dependent on a combination of the particular transcriptional regulatory elements that make up the gene's promoter and the different transcription factors that are present within the nucleus of the cell. As such, promoters are often classified as "constitutive", "tissue-specific", "cell-type-specific", or "inducible", depending on their functional activities in vivo or in vitro. For example, a constitutive promoter is one that is capable of directing transcription of a gene in a variety of cell types. Exemplary constitutive promoters include the promoters for the following genes which encode certain constitutive or "housekeeping" functions: hypoxanthine phosphoribosyl transferase (HPRT), dihydrofolate reductase (DHFR) [40]; adenosine deaminase, phosphoglycerate kinase (PGK), pyruvate kinase, phosphoglycerate mutase, the beta-actin promoter [41], and other constitutive promoters known to those of skill in the art. "Tissue-specific" or "cell-type-specific" promoters, on the other hand, direct transcription in some tissues and cell types but are inactive in others. Exemplary tissue-specific promoters include those promoters described in more detail herein below, as well as other tissue-specific and cell-type specific promoters known to those of skill in the art.

When used in the context of a promoter, the term "linked" as used herein refers to a physical proximity of promoter elements such that they function together to direct transcription of an operatively linked nucleotide sequence.

The term "purified" refers to an object species that is the predominant species present (i.e., on a molar basis it is more abundant than any other individual species in the composition). A "purified fraction" is a composition wherein the object species comprises at least about 50 percent (on a molar basis) of all species present. In making the determination of the purity of a species in solution or dispersion, the solvent or matrix in which the species is dissolved or dispersed is usually not included in such determination; instead, only the species (including the one of interest) dissolved or dispersed are taken into account. Generally, a purified composition will have one species that comprises more than about 80 percent of all species present in the composition, more than about 85%, 90%, 95%, 99% or more of all species present. The object species can be purified to essential homogeneity (contaminant species cannot be detected in the composition by conventional detection methods) wherein the composition consists essentially of a single species. A skilled artisan can purify a polypeptide of the presently disclosed subject matter using standard techniques for protein purification in light of the teachings herein. Purity of a polypeptide can be determined by a number of methods known to those of skill in the art, including for example, amino-terminal amino acid sequence analysis, gel electrophoresis, and mass-spectrometry analysis.

The terms "regulatory sequence" and "regulatory elements" are generic terms used throughout the specification to refer to polynucleotide sequences, such as initiation signals, enhancers, regulators, promoters (including minimal promoters), and termination sequences, which are necessary or desirable to affect the expression of coding and noncoding sequences to which they are operatively linked. Regulatory elements can comprise a promoter operatively linked to the nucleotide sequence of interest and termination signals. Exemplary regulatory sequences are described in Goeddel, 1990, and include, for example, the early and late promoters of simian virus 40 (SV40), adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase; e.g. Pho5, the promoters of the yeast alpha-mating factors, the polyhedron promoter of the baculovirus system and other sequences known to control the expression of genes of prokaryotic or eukaryotic cells or their viruses, and various combinations thereof [42]. The nature and use of such control sequences can differ depending upon the host organism. In prokaryotes, such regulatory sequences generally include promoter, ribosomal binding site, and transcription termination sequences. The term "regulatory sequence" is intended to include, at a minimum, components whose presence can influence expression, and can also include additional components whose presence is advantageous, for example, leader sequences and fusion partner sequences.

In certain embodiments, transcription of a polynucleotide sequence is under the control of a promoter sequence (or other regulatory sequence) that controls the expression of the polynucleotide in a cell-type in which expression is intended. It will also be understood that the polynucleotide can be under the control of regulatory sequences that are the same or different from those sequences which control expression of the naturally occurring form of the polynucleotide.

The term "reporter gene" refers to a nucleic acid comprising a nucleotide sequence encoding a protein that is readily detectable either by its presence or activity, including, but not limited to, luciferase, fluorescent protein (e.g. green fluorescent protein), chloramphenicol acetyl transferase, beta-galactosidase, secreted placental alkaline phosphatase, beta-lactamase, human growth hormone, and other secreted enzyme reporters. Generally, a reporter gene encodes a polypeptide not otherwise produced by the host cell, which is detectable by analysis of the cell(s); e.g. by the direct fluorometric, radioisotopic or spectrophotometric analysis of the cell(s) and typically without the need to kill the cells for signal analysis. In certain instances, a reporter gene encodes an enzyme, which produces a change in fluorometric properties of the host cell, which is detectable by qualitative, quantitative, or semiquantitative function or transcriptional activation. Exemplary enzymes include esterases, beta-lactamase, phosphatases, peroxidases, proteases (tissue plasminogen activator or urokinase) and other enzymes whose function can be detected by appropriate chromogenic or fluorogenic substrates known to those skilled in the art or developed in the future.

As used herein, the term "sequencing" refers to determining the ordered linear sequence of nucleic acids or amino acids of a DNA or protein target sample, using conventional manual or automated laboratory techniques.

As used herein, "significance" or "significant" relates to a statistical analysis of the probability that there is a non-random association between two or more entities. To determine whether or not a relationship is "significant" or has "significance," statistical manipulations of the data can be performed to calculate a probability, expressed as a "p-value." Those p-values that fall below a user-defined cutoff point are regarded as significant. In one example, a p-value less than or equal to 0.05, in another example less than 0.01, in another example less than 0.005, and in yet another example less than 0.001, are regarded as significant.

As used herein, the term "substantially pure" refers to that the polynucleotide or polypeptide is substantially free of the sequences and molecules with which it is associated in its natural state, and those molecules used in the isolation procedure. The term "substantially free" refers to that the sample is in some embodiments at least 50%, in some embodiments at least 70%, in some embodiments 80%, and in some embodiments 90% free of the materials and compounds with which is it associated in nature.

As used herein, the term "target cell" refers to a cell, into which it is desired to insert a nucleic acid sequence or polypeptide, or to otherwise effect a modification from conditions known to be standard in the unmodified cell. A nucleic acid sequence introduced into a target cell can be of variable length. Additionally, a nucleic acid sequence can enter a target cell as a component of a plasmid or other vector or as a naked sequence.

As used herein, the term "transcription" refers to a cellular process involving the interaction of an RNA polymerase with a gene that directs the expression as RNA of the structural information present in the coding sequences of the gene. The process includes, but is not limited to, the following steps: (a) the transcription initiation; (b) transcript elongation; (c) transcript splicing; (d) transcript capping; (e) transcript termination; (f) transcript polyadenylation; (g) nuclear export of the transcript; (h) transcript editing; and (i) stabilizing the transcript.

As used herein, the term "transcription factor" refers generally to a cytoplasmic or nuclear protein which binds to a gene, or binds to an RNA transcript of a gene, or binds to another protein which binds to a gene or an RNA transcript or another protein which in turn binds to a gene or an RNA transcript, so as to thereby modulate expression of the gene. Such modulation can additionally be achieved by other mechanisms; the essence of a "transcription factor for a gene" pertains to a factor that alters the level of transcription of the gene in some way. In some embodiments, the term "transcription factor" specifically refers to a protein that modulates gene expression by interaction with the transcriptional regulatory element and cellular components for transcription, including RNA Polymerase, Transcription Associated Factors (TAFs), chromatin-remodeling proteins, and any other relevant protein that impacts gene transcription.

The term "transcriptional regulatory sequence" or "transcriptional regulatory element," as used herein, each refers to a nucleotide sequence within the promoter region that enables responsiveness to a regulatory transcription factor. Responsiveness can encompass a decrease or an increase in transcriptional output and is mediated by binding of the transcription factor to the DNA molecule comprising the transcriptional regulatory element. In some embodiments, a transcriptional regulatory sequence is a transcription termination sequence, alternatively referred to herein as a transcription termination signal.

The term "transfection" refers to the introduction of a nucleic acid; e.g. an expression vector, into a recipient cell, which in certain instances involves nucleic acidmediated gene transfer. The term "transformation" refers to a process in which a cell's genotype is changed as a result of the cellular uptake of exogenous nucleic acid. For example, a transformed cell can express a recombinant form of a polypeptide of the presently disclosed subject matter or antisense expression can occur from the transferred gene so that the expression of a naturally occurring form of the gene is disrupted.

The term "vector" refers to a nucleic acid capable of transporting another nucleic acid to which it has been linked. One type of vector that can be used in accord with the presently disclosed subject matter is an episome; i.e., a nucleic acid capable of extra-chromosomal replication. Other vectors include those capable of autonomous replication and expression of nucleic acids to which they are linked. Vectors capable of directing the expression of genes to which they are operatively linked are referred to herein as "expression vectors." In general, expression vectors of utility in recombinant DNA techniques are often in the form of plasmids. In the present specification, "plasmid" and "vector" are used interchangeably as the plasmid is the most commonly used form of vector. However, the presently disclosed subject matter is intended to include such other forms of expression vectors which serve equivalent functions and which become known in the art subsequently hereto.

As used herein, the terms "transformed," "transgenic," and "recombinant" refer to a host organism such as a bacterium, animal, or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed," "non-transgenic," or "non-recombinant" host refers to a wild-type organism; e.g. a bacterium or plant, which does not contain the heterologous nucleic acid molecule.

As used herein, the term "transgenic animal" means a non-human animal having a non-endogenous (i.e., heterologous) nucleic acid sequence present as an extra-chromosomal element in a portion of its cells or stably integrated into its germ line DNA (i.e., in the genomic sequence of most or all of its cells). A heterologous nucleic acid is introduced into the germ line of such transgenic animals by genetic manipulation of, for example, embryos or embryonic stem cells of the host animal.

A "knock-out" of a gene means an alteration in the sequence of the gene that results in a decrease of function of the target gene, in some embodiments such that target gene expression is undetectable or insignificant in a cell, tissue, or organism. A knock-out of an endogenous gene means that function of one or more endogenous gene has been substantially decreased so that expression is not detectable or only present at insignificant levels. "Knock-out" transgenics can be transgenic animals having a heterozygous knock-out of an endogenous gene or a homozygous knock-out of an endogenous gene. "Knock-outs" also include conditional knock-outs, where alteration of the target gene can occur upon, for example, exposure of the animal to a substance that promotes target gene alteration, introduction of an enzyme that promotes recombination at the target gene site (e.g., the Cre in the Cre-lox system), or other method for directing the target gene alteration postnatally.

A "knock-in" of a target gene means an alteration in a host cell genome that results in altered expression (e.g. increased and/or ectopic) of the target gene, for example by introduction of an additional copy of the target gene, or by operatively inserting a regulatory sequence that provides for enhanced expression of an endogenous copy of the target gene.

"Knock-in" transgenics of interest for the presently disclosed subject matter can be transgenic animals having a knock-in of one or more genes mutated by the methods described. Such transgenics can be heterozygous for a knock-in of a mutated gene or homozygous for a knock-in of a mutated gene. "Knock-ins" also encompass conditional knock-ins as defined above.

Techniques for the preparation of transgenic animals are known in the art. Exemplary techniques are described for transgenic rats (U.S. Pat. No. 5,489,742); transgenic mice (U.S. Pat. Nos. 4,736,866, 5,550,316, 5,614,396, 5,625,125 and 5,648,061); transgenic pigs (U.S. Pat. No. 5,973,933); U.S. Pat. No. 5,162,215 (transgenic avian species), U.S. Pat. No. 5,741,957 (transgenic bovine species), and transgenic nematodes (Stinchcomb, et. al., see references).

Briefly, nucleotide sequences of interest are cloned into a vector (e.g. pLNK; Gorman et al., 1996), and the construct is transformed into a germ cell. In the germ cell, a chromosomal rearrangement event takes place wherein the nucleic acid sequences of interest are integrated into the genome of the germ cell by homologous recombination. Fertilization and propagation of the transformed germ cell results in a transgenic animal. Homozygosity of the mutation is accomplished by intercrossing.

Assays Generally.

In some embodiments, motility assays as described herein are based on directed movement, e.g. movement resulting from activation and/or inhibition of manipulated organismal mediators, such as chemo attractive/repulsive neurons. In some embodiments, movement results from laboratory manipulation of organismal mediators naturally implicated in motility. In some embodiments, movement results from laboratory manipulation of organismal mediators naturally implicated in processes other than organismal motility.

In some embodiments, motility assays as described herein are based on undirected and/or indirect movement such as a biased 'random walk'. For example, in some embodiments movement results from activation and/or inhibition of manipulated organismal mediators by virtue of their position within a gradient of one or more small molecules (chemical compounds). In some embodiments, movement in the desired direction results from the random movement that ceases in undesired directions, resulting in a net gain in the desired direction. In some embodiments, motility assays as described herein are based on both directed and undirected and/or indirect movement, as described herein. In some embodiments, the presence of a chemical gradient determines the direction of desired movement, whether by directed or undirected and/or indirect movement.

In some embodiments, assays are designed to determine, identify and/or isolate organisms and/or chemical compounds based on motility. In some embodiments, a pre-determined gradient of chemical and/or ions determines movement. In some embodiments, a pre-determined physical field determines movement, e.g. electromagnetic (phototropism), electrical (galvanotactic response), magnetic (magnetotactic response). In some embodiments, both a a pre-determined gradient of chemical and/or ions and a pre-determined physical field determines movement.

In some embodiments assays determine, identify, and/or isolate organisms and/or chemical compounds based on deviations in motility from pre-determined fields and/or gradients. In some embodiments assays determine, identify, and/or isolate organisms and/or chemical compounds based on deviations in motility from one pre-determined field and/or gradient relative to another pre-determined field and/or gradient. In some embodiments assays determine, identify, and/or isolate organisms and/or chemical compounds based on deviations in motility (e.g. galvanotactic) from a pre-determined physical field (e.g. electrical) due to a pre-determined chemical (and/or small molecule) gradient. In some embodiments assays determine, identify, and/or isolate organisms and/or chemical compounds based on deviations in motility (e.g. chemoattractive) from a pre-determined chemical (and/or small molecule) gradient due to a pre-determined physical field (e.g. electrical).

In some embodiments assays determine, identify, and/or isolate organisms and/or chemical compounds based on motility in the same direction as physical fields or pre-determined chemical and/or ionic gradients. In some embodiments assays determine, identify, and/or isolate organisms and/or chemical compounds based on motility in the opposite direction (or detectably different manners) as physical fields, or pre-determined chemical and/or ionic gradients. In some embodiments assays determine, identify, and/or isolate organisms and/or chemical compounds based on motility in an orthogonal direction relative to physical fields, or pre-determined chemical and/or ionic gradients. In some embodiments assays determine, identify, and/or isolate organisms and/or chemical compounds based on motility perpendicular (i.e. at a ninety degree angle) relative to physical fields, or pre-determined chemical and/or ionic gradients.

In some embodiments, organisms responding to chemicals are selected and/or screened for further analysis. For example, mutagenesis studies of an individual biopolymer (e.g. proteinaceous receptor) entails producing multiple strains of organisms each expressing wild-type and/or mutated biopolymer as described herein; exposing organisms to known chemicals allows for selection and/or screening of organisms. Selection (i.e. sensitive organisms are killed) results in live organisms or progeny of live organisms that can be utilized in further studies. Screening (e.g. motility assay) results in organisms with altered behavior that can be identified, and individual organisms displaying such behavior can be isolated.

In some embodiments, an organism of interest is immobilized by exposure to chemical. Immobilized organism(s) are separated, e.g. by robotic selection, or by removal of non-immobilized organism(s) (e.g. by exposure to mobility-inducing fields). In some embodiments, an organism of interest migrates towards or away from a source of chemical. In these embodiments, organism(s) of interest are separated based on position relative to known location of chemical or known location within chemical gradient, and/or organism (s) not migrating in a desired manner are removed and/or discarded (e.g. zonal separation).

In some embodiments, an organism is used to detect the presence and/or biological activity of chemicals. In these embodiments, organism behavior is used to indicate the spatial location of a chemical of interest. For example, an individual organism is placed in an assay whereby different chemicals are placed around the organism in a radial pattern. In one embodiment, the organism responds to chemical by migrating towards the source of chemical, identifying a chemical of interest. In one embodiment, the organism stops migrating at the physical location of a chemical source, identifying a chemical of interest. In one embodiment, the organism circles the physical location of a chemical source, identifying a chemical of interest.

In some embodiments, detection of chemical is indicated by activation of an alternative developmental pathway through a heterologously expressed biopolymer. In one embodiment, the organism ceases movement upon activation of said alternative developmental pathway. In one embodiment, the organism recovers from cessation of movement upon inhibition of a heterologously expressed biopolymer. In one embodiment the alternative developmental pathway is a diapause pathway and/or dauer pathway; entry into and/or exit from this pathway is used to identify sites of small molecule/biopolymer interaction(s), by the methods described herein.

In some embodiments, chemicals are known and selected for further analysis by the methods described herein. In some embodiments, chemicals are unknown and selected by the methods described herein. In some embodiments unknown chemicals are selected by the methods described herein and analyzed to determined chemical structure and/or chemical basis of activity.

Biopolymer Coupling.

In some embodiments, biopolymers (e.g. proteinaceous receptors) are heterologously expressed in chemosensory cells, and heterologously expressed biopolymers must functionally couple to cellular components that effect chemoattraction and chemorepulsion. Surprisingly, methods known in the art demonstrate efficient, functional coupling of heterologously expressed sequences to other cellular components within their new environment. This phenomenon has been observed for genes ectopically expressed within the same organism which they were derived from, and for genes orthologously expressed from one organism to another. While some heterologously expressed gene sequences are selected for limited interaction with cellular components (e.g. Green Fluorescent Protein), many genes retain their normal functional (e.g. catalytic and or signal transducing) effect in an ectopic environment.

In some embodiments, particular biopolymers (e.g. polypeptides and/or RNAs) are chosen for analysis by the methods described herein. Most—if not all—eukaryotic cells are thought to contain basic signal transduction components, including cell surface receptors, G-proteins, tyrosine kinases, adenylate cyclase, protein kinase A, protein kinase C, MAP kinase(s), CaM-kinases, and cyclic-nucleotide gated ion channels. High quality, on-going research efforts specifically seek to identify all components of chemosensory (e.g. taste and ofactory) cells responsible for mediating extracellular (environmental) signal(s).

In the absence of completed efforts in this regard, reasonable estimations for the general utility of methods described herein can still be made (i.e. which biopolymers can be studied). Introduction of heterologous components similar to the basic signal transduction components described in the scientific literature have a high probability of affecting chemosensation, either positively or negatively. Obviously, chemosensory-specific signal transduction components yet to be elucidated also have a high probability of affecting chemosensation, either positively or negatively. Characterizing small molecule inhibitors/activators by the methods described herein has a substantial likelihood of success when analyzing biopolymers (e.g. polypeptides and RNAs) implicated in chemosensory signal transduction.

Biopolymer Origin.

In some embodiments, heterologous components are analyzed by the methods described herein (i.e. components or biopolymers with an unknown relationship to endogenous cellular components or biopolymers). In some embodiments, endogenous cellular components are analyzed by the methods described herein. In some embodiments, exogenous cellular components are analyzed by the methods described herein (i.e. components or biopolymers not present endogenously). In some embodiments, homologous components are analyzed by the methods described herein (i.e. components or biopolymers substantially identical at the molecular level to endogenous cellular components and/or biopolymers).

In some embodiments, therapeutic target biopolymers (e.g. human-encoded proteins) are expressed heterologously in a manner described herein, or a similar manner, in an assay to test for the presence and/or efficacy of known and/or unknown small molecule (chemical) compounds. In some embodiments, therapeutic target biopolymers (e.g. human-encoded proteins) are expressed heterologously in a strain and/or genetic background deleted for one or more orthologous biopolymers naturally present in the organism in use, in a manner described herein, or a similar manner, in an assay to test for the presence and/or efficacy of known and/or unknown small molecule (chemical) compounds.

In some embodiments, therapeutic target biopolymers (e.g. human-encoded proteins) are expressed heterologously in a strain and/or genetic background deleted for one or more orthologous biopolymers naturally present in the organism in use and/or present within the same pathway, in a manner described herein, or a similar manner, in an assay to test for the presence and/or efficacy of known and/or unknown small molecule (chemical) compounds.

In some embodiments, therapeutic target biopolymers (e.g. human-encoded proteins) are expressed heterologously in a strain and/or genetic background deleted for one or more orthologous biopolymers naturally present in the organism in use and/or present within the same pathway for the purpose of increasing assay responsiveness and/or sensitivity, in a manner described herein, or a similar manner, in an assay to test for the presence and/or efficacy of known and/or unknown small molecule (chemical) compounds.

In some embodiments, therapeutic target biopolymers (e.g. human-encoded proteins) are expressed heterologously in a strain and/or genetic background duplicated and/or multimerized for one or more orthologous biopolymers naturally present in the organism in use and/or present within the same pathway for the purpose of increasing assay responsiveness and/or sensitivity, in a manner described herein, or a similar manner, in an assay to test for the presence and/or efficacy of known and/or unknown small molecule (chemical) compounds.

Uncoupled Biopolymers.

In some embodiments, heterologous sequences are introduced into chemosensory cells that are 'single-component' effectors of the sensory signal. For example, a heterologous ionotropic receptor is introduced into one or both classes of chemosensory cells (chemoattractive and chemorepulsive), and this 'single-component' biopolymer is capable of generating downstream signals (i.e. generating an action potential) effecting the desired behavior. In some embodiments, toxic and/or deleterious components are expressed heterologously, altering mobility. In these embodiments, small molecule (chemical compounds) are assayed to prevent constitutive and/or toxic and/or deleterious effects, as ascertained by the methods (e.g. assays) herein.

Chimeric Biopolymers.

In some embodiments, chimeric sequences are analyzed by the methods described herein. In some embodiments, chimeric sequences are generated between two heterologous components, and analyzed by the methods described herein. In some embodiments, chimeric sequences are generated between two endogenous components, and analyzed by the methods described herein. In some embodiments, chimeric sequences are generated between two exogenous components, and analyzed by the methods described herein. In some embodiments, chimeric sequences are generated between two homologous components, and analyzed by the methods described herein. In some embodiments, chimeric sequences are generated between endogenous components and exogenous components, and analyzed by the methods described herein. In some embodiments, activation domains of biopolymers are coupled to effector domains of different proteins, and analyzed by the methods described herein.

Biopolymer Analysis in Absence of Chemical.

In some embodiments, methods described herein introduce identical heterologous components into both chemoattractive and chemorepulsive sensory cells. In the absence of small molecule effectors under study, this specific embodiment identifies heterologous sequences that are capable of activity in both chemoattractive and chemorepulsive cellular environments, as ascertained by the organism becoming immobile or nearly immobile. Immobility can be induced by activation of cellular processes, inhibition of cellular processes, or by the induction of cellular degeneration and/or apoptosis. The class of "immobility-inducing" heterologous sequences that do not induce cellular degeneration and/or apoptosis represents a class of biomolecules with a substantial likelihood for successful implementation of the small molecule characterization methods described herein.

Primary and Secondary Detection of Chemical.

In some embodiments, a organism modified as described herein is used to detect the presence and/or biological activity of a known and/or unknown chemical (e.g. a small molecule and/or a biopolymer), i.e. in a primary (direct) manner. In some embodiments, a organism modified as described herein is used to detect the presence and/or biological activity of a known and/or unknown chemical (e.g. a small molecule and/or a biopolymer) produced by and/or present on the surface of and/or within a microorganism, i.e. in a secondary (indirect) manner. In some embodiments, an organism modified as described herein is used to detect the presence and/or biological activity of a chemical produced by and/or present on the surface of and/or within a natural microorganism. In some embodiments, an organism modified as described herein is used to detect the presence and/or biological activity of a chemical produced by and/or present on the surface of and/or within a microorganism engineered to produce said chemical. In some embodiments, an organism modified as described herein is used to detect the presence and/or biological activity of a chemical produced by and/or present on the surface of and/or within a microorganism engineered to produce said chemical, such as biopolymers produced in a "phage-display" by methods known in the art. In some embodiments, an organism modified as described herein is used to detect the presence and/or biological activity of a chemical produced by and/or present on the surface of and/or within a microorganism engineered to produce said chemical, such as metabolic intermediates and/or metabolic products generated by over-expression of metabolic enzymes, by methods known in the art. In some embodiments, an organism modified as described herein is used to detect the presence and/or biological activity of a chemical produced by and/or present on the surface of and/or within a microorganism engineered to produce said chemical, such as a chemical and/or biopolymer introduced from heterologous (e.g. human) sources, by methods known in the art. In some embodiments, an organism modified as described herein is used to detect the presence and/or biological activity of a chemical produced by and/or present on the surface of and/or within a microorganism engineered to produce said chemical, such as a chemical and/or biopolymer produced by heterologous (e.g. human) biopolymers (e.g. a heterologously introduced enzyme such as a steroid-processing and/or hormone-processing enzyme) by methods known in the art.

Organism Traits.

In some embodiments, an organism is chosen based on sensory attributes. In some embodiments, an organism is chosen based on the presence of both chemoattractive and chemorepulsive cells. In some embodiments, an organism is chosen based on cellular "equivalence" of chemosensory cells. For example, methods described herein have reduced assay 'noise' if sensory signal transduction components present in both chemoattractive and chemorepulsive cells are substantially identical (i.e. cells express and utilize substantially identical sets of genes in the signal transduction pathway). In some embodiments, defined genetic strains are chosen to provide a desired genetic 'background.'

In some embodiments, defined genetic strains of organisms are chosen to provide a desired genetic 'background' of chemosensory and chemorepulsive classes of sensory cells expressing substantially identical sets of genes. In some embodiments, an organism or a strain of an organism is chosen based on pre-determined sensory 'wiring'. In some embodiments, an organism or a strain of an organism is chosen based on pre-determined sensory 'mis-wiring.'

In some embodiments, laboratory strains known as 'wild-type' strains are employed to perform the methods described herein. In some embodiments, defined genetic mutant strains are employed to perform the methods described herein. In some embodiments, genetic mutations are introduced into strains to perform the methods described herein. In some embodiments, organisms are selectively bred to generate strains used to perform the methods described herein. In some embodiments, natural isolates of organisms are employed to perform the methods described herein.

In some embodiments, methods described provide an advantage over cell free assays by providing a common metric (motility) for testing numerous biopolymers (e.g. proteins). In some embodiments, dual-transformation and/or heterologous expression of pre-determined biopolymer provides an advantage over cellular assays by reducing background 'noise', i.e. activity due to cellular components ('genetic background') unrelated to the biopolymer of interest.

Assay Design.

A. Identifying Small Molecule(s).

In some embodiments, assays are performed for the purpose of detecting and/or identifying and/or isolating activators of biopolymers (e.g polypeptides or RNAs). In some embodiments, assays are performed for the purpose of detecting and/or identifying and/or isolating inhibitors of biopolymers (e.g polypeptides or RNAs). In some embodiments, assays are set up to observe chemoattraction in response to a desired chemical. In some embodiments, assays are set up to observe chemorepulsion in response to a desired chemical.

In some embodiments, a desired chemical compound activates a biopolymer in a chemoattractive cell (i.e. a cell that normally mediates chemoattractive signals in response to environmental stimuli), stimulating chemoattraction towards the source of the chemical. In some embodiments, a desired chemical compound inhibits a biopolymer in a chemoattractive cell (i.e. a cell that normally mediates chemoattractive signals in response to environmental stimuli), stimulating chemorepulsion from the source of the chemical.

In some embodiments, a desired chemical compound activates a biopolymer in a chemorepulsive cell (i.e. a cell that normally mediates chemorepulsive signals in response to environmental stimuli), stimulating chemorepulsion from the source of the chemical. In some embodiments, a desired chemical compound inhibits a biopolymer in a chemorepulsive cell (i.e. a cell that normally mediates chemoattractive signals in response to environmental stimuli), stimulating chemoattraction towards the source of the chemical.

In some embodiments, a desired chemical compound activates a biopolymer in a chemoattractive cell (i.e. a cell that normally mediates chemoattractive signals in response to environmental stimuli), and simultaneously and/or sequentially inhibits a biopolymer in a chemorepulsive cell (i.e. a cell that normally mediates chemoattractive signals in response to environmental stimuli), stimulating chemoattraction towards the source of the chemical.

In some embodiments, a desired chemical compound inhibits a biopolymer in a chemoattractive cell (i.e. a cell that normally mediates chemoattractive signals in response to environmental stimuli), and simultaneously and/or sequentially activates a biopolymer in a chemorepulsive cell (i.e. a cell that normally mediates chemorepulsive signals in response to environmental stimuli), stimulating chemorepulsion from the source of the chemical.

In some embodiments, a desired chemical compound activates a biopolymer in a chemoattractive cell (i.e. a cell that normally mediates chemoattractive signals in response to environmental stimuli), and simultaneously and/or sequentially activates a biopolymer in a chemorepulsive cell (i.e. a cell that normally mediates chemorepulsive signals in response to environmental stimuli), resulting in an immobile or nearly immobile organism. This embodiment demonstrates results obtained when identical biopolymers are expressed in both chemoattractive and chemorepulsive cells.

In some embodiments, a desired chemical compound inhibits a biopolymer in a chemoattractive cell (i.e. a cell that normally mediates chemoattractive signals in response to environmental stimuli), and simultaneously and/or sequentially inhibits a biopolymer in a chemorepulsive cell (i.e. a cell that normally mediates chemoattractive signals in response to environmental stimuli), resulting in an immobile or nearly immobile organism. This embodiment demonstrates results obtained when identical biopolymers are expressed in both chemoattractive and chemorepulsive cells.

In embodiments where identical biopolymers are expressed in both chemoattractive and chemorepulsive cells, novel small molecule chemical compounds can be identified by assaying for organisms made immobile or nearly immobile in response to addition of chemical(s).

In some embodiments, one, more than one, or a plurality of known (pre-determined) or unknown chemicals is detected and/or identified and/or isolated interacting with a pre-determined biopolymer by the methods described herein.

In some embodiments, one or more than one known (pre-determined) or unknown biopolymer is detected and/or identified and/or isolated interacting interacting with a pre-determined chemical by the methods described herein.

In some embodiments, one or more than one known (pre-determined) or unknown biopolymer is detected and/or identified and/or isolated interacting interacting with one, more than one, or a plurality of known (pre-determined) or unknown chemicals by the methods described herein.

In some embodiments, one or more than one known (pre-determined) or unknown biopolymer is detected and/or identified and/or isolated interacting interacting with one, more than one, or a plurality of known (pre-determined) or unknown chemicals by the methods described herein.

In embodiments where identical biopolymers are expressed in both chemoattractive and chemorepulsive cells, novel small molecule chemical compounds can be identified by assaying for organisms regaining normal motility upon removal of chemical(s).

In some embodiments, assays are performed not utilizing immobile or nearly immobile organisms, but with organisms with normal motility that is augmented or diminished by activation and/or inhibition of chemosensory responses.

In some embodiments, sensory cells are not chemosensory, but respond naturally to other sensory stimuli (e.g. mechanosensory, thermosensory). In these embodiments, expression of heterologous sequence converts non-chemosensory cells into chemosensory cells. In some embodiments, sensory cells are not utilized, however interneurons or motor neuron are utilized instead. In these embodiments, expression of heterologous sequence converts non-sensory cells into chemosensory cells.

B. Assay Construction.

In some embodiments, a single source of chemical ligand is utilized. In some embodiments, multiple sources of chemical ligands are utilized. In some embodiments, assays are performed with a single chemical species. In some embodiments, assays are performed with multiple chemical species. In some embodiments, assays measure linear motility in response to chemical(s). In some embodiments, assays measure circular motility in response to chemical(s). In some embodiments, assays measure oscillating motility in response to chemical(s).

In some embodiments, assays are designed as a linear track. In some embodiments, assays are designed as a circular track. in some embodiments, assays represent a radial array. In some embodiments, assays represent a spiral array. In some embodiments assays represent a polygonal array, such as a rectangular and/or square array. In some embodiments, assays represent a three dimensional array. In some embodiments, assays represent a three dimensional spherical array. In some embodiments, assays represent a three dimensional polygonal array, such as a cubic array.

In some embodiments, chemical(s) remain in a fixed location. In some embodiments, chemicals(s) are mobile. In some embodiments, chemical(s) are in a mobile phase. In some embodiments, chemicals in a mobile liquid phase. In some embodiments, chemicals are in a mobile gas phase.

In some embodiments, chemical(s) are added to a carrier phase. In some embodiments the carrier phase is liquid. In some embodiments the carrier phase is gaseous. In some embodiments, chemical(s) are adsorbed onto solid surfaces. In some embodiments, chemical(s) are adsorbed onto gelatinous support. In some embodiments, chemical(s) are adsorbed onto agar. In some embodiments, chemical(s) are adsorbed onto agarose. In some embodiments, chemical(s) are adsorbed onto polyacrylamide. In some embodiments, chemical(s) are maintained in capillaries.

In some embodiments, chemical(s) are present as a point source relative to organisms. In some embodiments chemical(s) are in a linear array relative to organisms. In some embodiments chemical(s) are in a circular array relative to organisms. In some embodiments, chemicals(s) are in a three-dimensional array relative to organisms.

In some embodiments, organisms are present as a point source relative to chemical(s). In some embodiments, organisms are present in a linear array relative to chemical(s). In some embodiments, organisms are present in a circular array relative to organisms. In some embodiments, organisms are present in a three dimensional array relative to chemical(s).

In some embodiments chemical(s) are fixed, while organisms are mobile. In some embodiments, chemical(s) are mobile while organisms are fixed. In some embodiments, chemical(s) and organisms are mobile. In some embodiments, chemical(s) and organisms are fixed.

In some embodiments, organisms are restrained. In some embodiments, organisms are challenged with chemical(s), and organismal responses are assayed. In some embodiments, organisms are challenged with chemical(s), and organismal movement is recorded. In some embodiments, organisms are challenged with chemical(s), and organismal movement is recorded using physical transducers. In some embodiments, organisms are challenged with chemical(s), and/or movement is recorded using pressure transducers.

In some embodiments, chemical(s) and organisms move towards each other. In some embodiments, chemical(s) and organisms move away from each other. In some embodiments, chemical(s) and organisms move at an angle to each other. In some embodiments, chemical(s) and organisms move perpendicular to each other. In some embodiments, chemical(s) and organisms move parallel to each other. In some embodiments, chemical(s) and organisms move parallel towards each other. In some embodiments chemical(s) and organisms move parallel away from each other. In some embodiments, chemical(s) and organisms move in a counter-current fashion relative to each other.

In some embodiments, chemical species are assayed individually. In some embodiments, chemical species are assayed en masse. In some embodiments, chemicals are assayed simultaneously. In some embodiments, chemicals are assayed sequentially. In some embodiments, chemicals are assayed batch-wise.

In some embodiments, chemical species are made bioavailable by the addition of other substances, e.g. carrier compounds ("vehicles" such as DMSO) or structures (e.g. liposomes).

In some embodiments, chemical species are made bioavailable by the use of specialized strains of organism. In some embodiments, chemical species are made bioavailable by the use of specialized strains of nematodes. In some embodiments, chemical species are made bioavailable by the use of specialized strains of the nematode *C. elegans*.

In some embodiments, chemical species are made bioavailable by the use of specialized strains of organisms that increase chemical uptake to improve organismal sensitivity to chemical. In some embodiments, chemical species are made bioavailable by the use of specialized strains of nematodes that increase chemical uptake to improve organismal sensitivity to chemical. In some embodiments, chemical species are made bioavailable by the use of specialized strains of the nematode *C. elegans* that increase chemical uptake to improve organismal sensitivity to chemical.

In some embodiments, chemical species are made bioavailable by the use of specialized strains of organisms that display components on the organismal surface to improve organismal sensitivity to chemical.

In some embodiments, an organism is assayed individually. In some embodiments, multiple individual organisms of the same species are assayed. in some embodiments, multiple individual organisms of different species are assayed. In some embodiments, organisms are assayed simultaneously. In some embodiments, organisms are assayed sequentially. In some embodiments, organisms are assayed batch-wise.

In some embodiments, the methods described herein comprise an organism comprising a nervous system modified to express said biopolymer.

In some embodiments, the methods described herein comprise an organism comprising a chemosensory system modified to express said biopolymer.

In some embodiments, the methods described herein comprise an organism comprising a chemosensory system comprising said oppositely directed mediators of movement modified to express said biopolymer.

In some embodiments, the methods described herein comprise a nematode organism modified to express said biopolymer. Emphasizing the focus on expressing said biopolymer to co-opting natural chemosensory processes as described herein, such an embodiment can be referred to as a Nematode chemosensory-based and/or Olfactory-based Structural Elucidation assay, or NOSE assay.

In some embodiments, the methods described herein comprise a nematode species modified to express said biopolymer selected from the group consisting of *Caenorhabditis briggsae, Caenorhabditis remanei, Pristiochus pacificus, Heterorhabditis bacteriophora*, and *Steinernema carpocapsae*.

In some embodiments, the methods described herein comprise the nematode species *Caenorhabditis elegans* modified to express said biopolymer.

In some embodiments, the methods described herein comprise the organism *Drosophila melanogaster* modified to express said biopolymer.

In some embodiments, the methods described herein comprise a nematode organism modified to express said biopolymer in said nervous system.

In some embodiments, the methods described herein comprise a nematode organism modified to express said biopolymer in said chemosensory system.

In some embodiments, the methods described herein comprise a nematode organism modified to express said biopolymer in said chemosensory system comprising said oppositely directed mediators of movement.

In some embodiments, the methods described herein comprise a nematode organism modified to express said biopolymer in olfactory cells of said chemosensory system.

In some embodiments, the methods described herein comprise a nematode organism modified to express said biopolymer in soluble factor chemosensory cells of said chemosensory system.

In some embodiments, the methods described herein comprise a nematode organism modified to express said biopolymer in olfactory cells of said chemosensory system, said oppositely-directed cells comprising one or more chemoattractive cells selected from the group consisting of AWA and AWC cells.

In some embodiments, the methods described herein comprise a nematode organism modified to express said biopolymer in olfactory cells of said chemosensory system, said oppositely-directed cells comprising one or more chemorepulsive cells selected from the group consisting of AWB, ASH, and ADL cells.

In some embodiments, the methods described herein comprise a nematode organism modified to express said biopolymer in soluble factor chemosensory cells of said chemosensory system, said oppositely-directed cells comprising one or more chemoattractive cells selected from the group consisting of ASE, ADF, ASG, ASI, and ASK cells.

In some embodiments, the methods described herein comprise a nematode organism modified to express said biopolymer in soluble factor chemosensory cells of said chemosensory system, said oppositely-directed cells comprising one or more chemorepulsive cells selected from the group consisting of ASH and ADL cells.

In some embodiments, the methods described herein comprise one or more cells chosen from the group consisting of AWA and AWC cells, and one or more cells chosen from the group consisting of AWB, ASH, and ADL cells.

In some embodiments, the methods described herein comprise one or more cells chosen from the group consisting of ASE, ADF, ASG, ASI, and ASK cells, and one or more cells chosen from the group consisting of ASH and ADL cells.

In some embodiments, the methods described herein comprise a nematode organism modified to express said biopolymer in chemosensory cells of said chemosensory system, said oppositely-directed cells comprising one or more chemo-modulatory cells selected from the group consisting of ADF, ASI, and ASG cells.

In some embodiments, the methods described herein comprise a nematode organism modified to express said biopolymer in chemosensory cells of said chemosensory system, said oppositely-directed cells comprising one or more chemo-modulatory cells selected from the group consisting of ASJ cells.

In some embodiments, the methods described herein comprise one or more cells chosen from the group consisting of ADF, ASI, and ASG cells, and one or more cells chosen from the group consisting of ASJ cells.

In some embodiments, the methods described herein comprise expressing a natural biopolymer and the same biopolymer containing a point mutation in oppositely-directed mediators of movement.

In some embodiments, the methods described herein comprise expressing mutated biopolymer in both oppositely-directed mediators of movement.

In some embodiments, the methods described herein comprise expressing reciprocal chimeric biopolymers in oppositely-directed mediators of movement.

In some embodiments, the methods described herein comprise expressing differentially mutated biopolymers in oppositely-directed mediators of movement.

In some embodiments, the methods described herein comprise expressing homologous biopolymers in oppositely-directed mediators of movement.

In some embodiments, the methods described herein comprise expressing orthologous biopolymers in oppositely-directed mediators of movement.

In some embodiments, the methods described herein comprise expressing unrelated biopolymers in oppositely-directed mediators of movement.

In some embodiments, the methods described herein comprise expressing mutated and/or recombined homologous, orthologous and/or unrelated biopolymers in oppositely-directed mediators of movement.

Specific Embodiments:

Embodiments described in this section are meant to be representative and not exhaustive. General descriptions of how methods described herein may be utilized in the pharmaceutical industry are envisaged. Biopolymers, components, genes, organisms, strains, and assay design are expected to be tailored to the individual technical challenge presented in an industry setting: descriptions below are merely representative.

Primary Embodiment: Expression of Identical or Nearly Identical Components

A known human signal transduction component is heterologously expressed as described herein. Components include subunits of heterotrimeric GTPase proteins, ras, rho, p53, p21. Because of the similarity of signal transduction mechanisms across phyla, the heterologously-expressed component naturally 'couples' to pre-existing cellular effectors in the new cellular environment. Signal 'strength' may be improved by utilizing strains deleted for endogenous, orthologous components (i.e. genes performing an identical function in the assayable organism). In the first instance, chemical compounds (drug candidates) are selected by expressing identical components in paired sets of mediators of movement (forward-directed and backward-directed chemosensory or motor neurons), and assaying for chemical-induced immobility. This methodology is employed to obtain drug candidates for known or unknown components.

In the second instance, antagonistic chemical compounds (drug candidates) are selected against mutated signal transduction components. A mutated form of the signal transduction component is expressed in a backward-directed mediator (neuron), while the un-mutated form of the signal transduction component is heterologously expressed in forward-directed mediator (neuron). This methodology may be employed when the activity of a mutated component is known to cause human disease. Examples of mutated signal transduction components include mutated ras (reviewed in Cox and Der, 2002), and/or mutated Galpha-s or Galpha-q (Kalinec et. al., 1992; Landis et. al., 1989).

An assay is performed in a radial array, with test organisms in the center of a circle. At the perimeter of the circle are placed known and unknown chemicals, and a gradient of chemical spreads towards the test organisms at the center of the circle. A chemical (drug candidate) that inhibits activity of the mutated signal transduction component in backward-directed neurons will exhibit a net forward movement towards that chemical. Chemicals identified in this manner are demonstrably more active on mutated components than un-mutated components, and may prove to be potent anti-cancer and/or anti-degenerative agents.

Primary Embodiment: Expression of Dissimilar Components

A known human ion channel is heterologously expressed as described herein. The ion channel of interest is expressed a neuron mediating (i.e. controlling) backward movement. In a simple example, the ion channel of interest activates (promotes) backward-directed movement, either in its natural state, or mutated to cause constitutive activation of backward movement. Addition of known or unknown chemical capable of inhibiting the ion channel of interest relieves constitutive backward-directed and/or coiling movement, and the animal is capable of moving forward. Chemicals identified in this manner are drug candidates.

Known and/or unknown chemicals can be identified in this manner, however the assay become much more robust if a related ion channel receptor is expressed in a neuron mediating forward-directed movement (dual transformation). For example, dopaminergic neurons express different classes of dopamine receptor subunits in different tissues (reviewed in Seeman and Van Tol, 1993). Receptors of the D4 class have been linked to disease such as schizophrenia, however, isolating chemical compounds (e.g. small molecules, drug candidates) specifically against D4 receptor subtypes is problematic, because of the presence of other subunits within the same cell and/or tissue. However, if receptors of different classes of receptors are expressed in different cells mediating opposite behaviors (e.g. forward and backward movement; forward movement and immobility), chemical sensitivity of different receptors to the same chemical can be observed.

By expressing a receptor of the D4 class in backward-directed neurons and receptors of a non disease-associated dopamine receptor class (e.g. D1 class, for exemplary purposes) in forward-directed neurons, chemical compounds that act on D4 receptors can be differentiated from chemical compounds that act on D1 receptors. In the example given (expressing a D4 receptor in neuron mediating backward motion), expression of a D1 receptor subtype (class) in a neuron mediating forward movement creates a single, assayable organism and/or assayable strain. Chemicals will be identified that fall into two desired classes: those that result in dopaminergic receptor-mediated backward movement, and those that result in dopaminergic receptor-mediated forward movement.

In a typical embodiment, a linear assay is employed. Identical test organisms are placed on a line, and different candidate chemicals are placed on a parallel line a short distance away. Chemicals that result in dopaminergic receptor-mediated forward movement can be easily identified and differentiated from chemicals that result in dopaminergic receptor-mediated backward movement.

Four simple scenarios can be envisaged. Chemical compounds that inhibit D4-mediated (backward-directed) mobility while simultaneously having no effect on D1-mediated (forward-directed) mobility will result in increased forward movement. Chemical compounds that activate D4-mediated (backward-directed) mobility while simultaneously having no effect on D1-mediated (forward-directed) mobility will result in increased backward movement. Chemical compounds that activate D1-mediated (forward-directed) activity while simultaneously having no effect on D4-mediated (backward-directed) movement will result in increased forward movement. Chemical compounds that inhibit D1-mediated (backward-directed) movement will result in increased backward movement.

By the examples given, chemicals that mediate increased forward movement either activate D1 receptor subtypes, or inhibit D4 receptor subtypes. Chemicals that mediate increased backward movement either activate D4 receptor subtypes, or inhibit D1 receptor subtypes. Chemical activity can be distinguished (activating vs. inhibiting) using the methods described herein, for example, by comparing results obtained with strains expressing receptor in neurons directing either forward or backward movement, but not both. Site(s) of chemical activity can be further elucidated by determining if a chemical acts on a certain receptor site of interest, by mutating receptor at that site, and performing assays ('nearly identical' biopolymer assays) as described herein. Chemicals identified by the methods described herein can be tested and/or confirmed in other assays such as heterologous expression assays (e.g. *Xenopus* oocyte expression), to elucidate particular molecular mechanisms, (e.g. competitive, non-competitive, uncompetitive inhibition, ligand occlusion, receptor de-sensitization, etc.).

Drug candidates identified in this pharmacogenomic manner hold great promise for treatment of specific disease allele gene products, without affecting normal allele gene products. Examples include inherited or spontaneous oncogenic alleles, inherited or spontaneous metabolically-deficient alleles (e.g. sickle cell anemia), and inherited or spontaneous degenerative alleles (e.g. ApoE alleles implicated in Alzheimer's Disease). In alternative implementations, drug candidates can be isolated that are effective on biopolymers from infective and/or parasitic organisms, but have no effect on orthologous biopolymers present in a host organism. Examples of infective and/or parasitic organisms include bacteria, protozoa, trypanosomes, yeast and other fungi, parasitic nematodes, and virallyencoded gene products. Examples of host organisms include humans, animals of agricultural/veterinary/environmental importance, and plants of agricultural/environmental importance.

Primary Embodiment: Expression of Recombined Components

In some embodiments, a particular protein domain is so therapeutically important that mapping its structure and sequence tolerance is of utmost importance for therapeutic intervention. An example is ATP binding domains of cellular kinases, which have been utilized to generate a number of important pharmacological compounds. The most well known of these compounds is imatinib mesylate (trade name, Gleevec), which is used for treating Chronic Myelogenous Leukemia, or CML (O'Dwyer, et. al. 2003). CML can be caused by a chromosome translocation producing a recombined kinase, bcr-abl, which causes uncontrolled cell growth. imatinib mesylate inhibits bcr-abl by a mechanism whereby imatinib mesylate is believed to interfere with ATP binding in the abl ATP-binding domain, although imatinib mesylate is known to interact with other cellular kinases (e.g. c-kit).

ATP-binding domains are of such critical importance in cellular growth and differentiation that the methods described herein may be essential in deciphering small molecule binding to this important, conserved domain. In a specific embodiment, bcr-abl is expressed in neurons directing forward movement, c-kit is expressed in neurons directing backward movement. The addition of imatinib mesylate to the assayable organism described results in alterations in mobility and/or cessation of mobility. The two genes under study, bcr-abl and c-kit, are then recombined, producing 'crossover' alleles (reciprocal translocations) in the ATP-binding domain. These 'crossover' alleles are examined to determine the point of crossover, and the effect on organismal mobility by expressing each of the crossover alleles in neurons as described. For example, if a set of crossover alleles results in increased forward movement, then the ATP-binding domain of the allele in the neuron directing forward movement has been altered to reduce or obviate imatinib mesylate binding, and/or the ATP-binding domain of the allele in the neuron directing backward movement has been altered to increase or stabilize imatinib mesylate binding.

Assays are performed as described herein. In a typical embodiment, multiple different recombined alleles are made, and multiple different dually-transformed organismal strains are constructed containing pairs of recombined alleles in appropriate mediators of movement. Organisms containing recombined heterologously-expressed alleles are placed at the perimeter of a circle radius r, and a test chemical (e.g. imatinib mesylate) is placed at the center of the circle. Control organisms (un-recombined alleles) can be placed on the perimeter of the same circle radius r (e.g. at 0, 90, 180, and 270 degrees), to provide visual reference for alterations in mobility seen in organisms containing recombined alleles. Organisms exhibiting altered mobility are recovered, and their alleles analyzed (e.g. DNA sequencing).

Reciprocal translocations can be recombined repeatedly, producing subdomains or 'patches' of crossed-over sequence. These subdomains can be repeatedly generated and tested for imatinib mesylate binding activity, until a consensus binding subdomain is identified. As an ultimate test, the identified subdomain can be tested to determine if imatinib mesylate binding is conferred on an unrelated biopolymer. Using the pair-wise methodology described, numerous other ATP-binding proteins may be tested in a similar manner, until a family-wide consensus binding subdomain is identified (e.g. src kinase, EGF receptor, PDGF receptor, FGF receptor, etc.).

Once a consensus (e.g. imatinib mesylate) binding domain has been established, second generation therapeutic compounds can be generated that are more specific for one domain of therapeutic interest (e.g. ATP-binding domain). This can easily be accomplished by expressing a consensus (recombined) domain in a cell (e.g. neuron) directing forward movement, while the specific biopolymer (drug target candidate) is expressed in a cell (e.g. neuron) directing backward movement. Specific inhibition of the drug target candidate in neurons directing backward movement without inhibition of the consensus (recombined) domain expressed in neurons directing forward movement results in increased motility towards a source of chemical with these properties.

In a typical embodiment, test organisms are placed at the center of a circle, and small molecules (chemical compounds) that are potential drug candidates are placed at the perimeter of the circle, radius r. Chemicals produce a gradient of concentration which, if effective on heterologously-expressed alleles, causes migration of test organisms towards chemicals with desired activity. An assay improvement is to use a strain of organism that results in organismal 'coiling' when moving backwards, not a linear backward movement.

Numerous gene families and numerous conserved protein domains can be analyzed by these methods. Different first generation therapeutics, different families of candidate drug targets, and different specific drug targets can be examined to identify novel therapeutics. Thus novel therapeutics can be detected and/or identified and/or isolated by a general strategy employing the methods described herein.

While the foregoing describes what are presently believed to be representative and preferred embodiments of the invention, those skilled in the art will realize that other changes and modifications may be made thereto without departing from the spirit of the invention, and we claim all such changes and modifications as falling within the true and/or complete scope of the invention.

REFERENCES

The references listed below as well as all references cited in the specification are incorporated herein by reference to the extent that they supplement, explain, provide a background for, or teach methodology, techniques, and/or compositions employed herein.

1 Mello, C. and A. Fire (1995). "DNA transformation." Methods Cell Biol 48: 451-82.
2 Mello, C. C., J. M. Kramer, et al. (1991). "Efficient gene transfer in *C. elegans*: extrachromosomal maintenance and integration of transforming sequences?" Embo J 10(12): 3959-70.
3 Sambrook, J. and D. W. Russell (2001). Molecular cloning: a laboratory manual. Cold Spring Harbor, N.Y., Cold Spring Harbor Laboratory Press.
4 Scharfmann, R., J. H. Axelrod, et al. (1991). "Long-term in vivo expression of retrovirus-mediated gene transfer in mouse fibroblast implants." Proc Natl Acad Sci USA 88(11): 4626-30.
5 Stinchcomb, D. T., J. E. Shaw, et al. (1985). "Extrachromosomal DNA transformation of *Caenorhabditis elegans*." Mol Cell Biol 5(12): 3484-96.
6 U.S. Pat. No. 4,736,866.
7 U.S. Pat. No. 5,162,215.
8 U.S. Pat. No. 5,489,742.
9. U.S. Pat. No. 5,550,316.
10 U.S. Pat. No. 5,573,933.
11 U.S. Pat. No. 5,614,396.
12 U.S. Pat. No. 5,648,061.
13 U.S. Pat. No. 5,741,957.
14 Williams, R. S., J. A. Thomas, et al. (1993). "Human heat shock protein 70 (hsp70) protects murine cells from injury during metabolic stress." J Clin Invest 92(1): 503-8.

TABLE OF ABBREVIATIONS

5'-UTR—5'-untranslated region
cDNA—complementary DNA
CMV—cytomegalovirus
DHFR—dihydrofolate reductase
DNA—deoxyribonucleic acid
dsRNA—double stranded ribonucleic acid
DTPA—diethylenetriamine pentaacetic acid
EDTA—ethylenediamine tetraacetic acid
EGTA—ethyleneglycol tetraacetic acid
FACS—Fluorescence Activated Cell Sorting
FRET—fluorescence resonance energy transfer
G418—an aminoglycoside antibiotic
GFP—green fluorescent protein
HPRT—hypoxanthine phosphoribosyl transferase
hsp—heat shock protein
HSV-tk—herpes simplex virus thymidine kinase
IRES—internal ribosome entry site
LCR—Ligase Chain Reaction
MAR—matrix attachment region
miRNAs—micro ribonucleic acids ORF—open reading frame
PAB—poly-A binding protein
PCR—polymerase chain reaction
PGK—phosphoglycerate kinase
RNA—ribonucleic acid
RNAi—RNA interference
SAGE—serial analysis of gene expression
SAR—scaffold attachment region
SDS—sodium dodecyl sulfate
SSC—standard saline citrate
SSH—suppression subtraction hybridization
SV40—simian virus 40
TAFs—Transcription Associated Factors
$T_m$—thermal melting point
UTR—un-translated region
XIST—X chromosome inactivation transcript

What is claimed:

1. A process for detecting a molecular interaction between a small molecule and a first pre-determined receptor in the presence of a second pre-determined receptor, the process comprising:
   (a) providing a transgenic *C. elegans* modified to express a first pre-determined receptor in a first neuron that directs movement in a first direction while simultaneously expressing a second pre-determined receptor that is a different receptor from said first pre-determined receptor or is a mutated version of said first pre-determined receptor in a second neuron that directs movement in a second direction, wherein said second direction is opposite said first direction;
   (b) placing said transgenic *C. elegans* in an electrical field and exposing said transgenic C, *elegans* to said small molecule in a gradient of the small molecule; wherein said electrical field is oriented in a direction that is different from a direction of said gradient of said small molecule; and
   (c) ascertaining a change in mobility of the transgenic *C. elegans* in response to said exposing step,
   wherein said change in mobility is indicative of a molecular interaction between said small molecule and said first pre-determined receptor despite the presence of said second pre-determined receptor.

2. The method of claim 1, wherein said transgenic *C. elegans* expresses said first and second pre-determined receptors in its chemosensory system.

3. The method of claim 2, wherein said first and second neurons are oppositely directed mediators of movement present in chemosensory system of the transgenic *C. elegans*.

4. The method of claim 1, wherein said first pre-determined receptor is a naturally occurring receptor and said second pre-determined receptor is a modified version of the first pre-determined receptor containing a point mutation, and further wherein the first and the second pre-determined receptors are expressed in oppositely-directed mediators of movement.

5. The method of claim 1, wherein said first pre-determined receptor and said second pre-determined receptor are different members of the same receptor gene family.

6. The method of claim 5, wherein said first pre-determined receptor and said second pre-determined receptor are different members of the same human receptor gene family.

7. The method of claim 1, wherein said small molecule causes a change in mobility of said transgenic *C. elegans* in said electrical field relative to mobility of said transgenic *C. elegans* in said electrical field but with said small molecule not present.

* * * * *